US009809642B2

(12) United States Patent
Leighton et al.

(10) Patent No.: US 9,809,642 B2
(45) **Date of Patent: *Nov. 7, 2017**

(54) TRANSGENIC CHICKEN COMPRISING AN INACTIVATED IMMUNOGLOBULIN GENE

(71) Applicant: Crystal Bioscience Inc., Emeryville, CA (US)

(72) Inventors: Philip A. Leighton, San Francisco, CA (US); William Don Harriman, Alameda, CA (US); Robert Etches, Oakland, CA (US)

(73) Assignee: Crystal Bioscience Inc., Emeryville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/167,876

(22) Filed: May 27, 2016

(65) Prior Publication Data

US 2016/0297871 A1 Oct. 13, 2016

Related U.S. Application Data

(63) Continuation of application No. 14/114,159, filed as application No. PCT/US2012/039191 on May 23, 2012, now Pat. No. 9,380,769.

(60) Provisional application No. 61/489,638, filed on May 24, 2011.

(51) Int. Cl.

| | |
|---|---|
| ***C07K 16/00*** | (2006.01) |
| ***A01K 67/027*** | (2006.01) |
| ***C12N 15/90*** | (2006.01) |

(52) U.S. Cl.

CPC .......... *C07K 16/00* (2013.01); *A01K 67/0276* (2013.01); *C12N 15/902* (2013.01); *A01K 2217/075* (2013.01); *A01K 2217/15* (2013.01); *A01K 2227/30* (2013.01); *C07K 2317/14* (2013.01); *C07K 2317/24* (2013.01); *C07K 2317/51* (2013.01)

(58) Field of Classification Search

None

See application file for complete search history.

(56) References Cited

U.S. PATENT DOCUMENTS

| | | | |
|---|---|---|---|
| 6,114,598 | A | 9/2000 | Kucherlapati et al. |
| 9,380,769 | B2 * | 7/2016 | Leighton ............ A01K 67/0276 |
| 2002/0028488 | A1 | 3/2002 | Singh et al. |
| 2003/0182675 | A1 * | 9/2003 | Etches .................. C07K 16/00 800/19 |
| 2010/0138946 | A1 | 6/2010 | Van De La Voir et al. |

FOREIGN PATENT DOCUMENTS

| | | |
|---|---|---|
| WO | WO2003081992 | 10/2003 |
| WO | WO2009023800 | 2/2009 |
| WO | WO2011019844 | 2/2011 |

OTHER PUBLICATIONS

Kim et al., Biol Reprod (2010) 82 (2): 257-262.*

Adachi, et al. "Gene targeting using the human Nalm-6 pre-B cell line", BioScience Trends 2008; 2(5):169-180.

Database Accession No. M30320, "Gallus gallus Ig germline heavy chain J segment (JH) gene.", 1994, 1 page.

Hillier et al., "Sequence and comparative analysis of the chicken genome provide unique perspectives on vertebrate evolution", Nature, 2004, 432:695-716.

Lillico, et al. "Transgenic chickens as bioreactors for protein-based drugs", Drug Discov. Today, Feb. 1, 2005;10 (3):191-6.

Meek, et al. "Efficient Gene Targeting by Homologous Recombination in Rat Embryonic Stem Cells", PLoS ONE 1 NWW. plosone_org, Dec. 2010, vol. 5, Issue 12, e14225, pp. 1-6.

Reynaud, et al., "Somatic hyperconversion diversifies the single VH gene of the chicken with a high incidence in the D region", vol. 59, No. 1,1989, pp. 171-183.

Sakurai, et al. "Efficient integration of transgenes into a defined locus in human embryonic stem cells", Nucleic Acids Research, 2010, vol. 38, No. 7, e96, pp. 1-8.

Tong, et al. "Production of p53 gene knockout rats by homologous recombination in embryonic stem cells", Nature, vol. 467, 2010, pp. 211-215.

* cited by examiner

*Primary Examiner* — James Douglas Schultz

(74) *Attorney, Agent, or Firm* — James S. Keddie; Bozicevic, Field & Francis LLP

(57) ABSTRACT

A transgenic chicken comprising an inactivated heavy immunoglobulin gene and/or inactivated light chain immunoglobulin gene is provided, as well as cells and targeting vectors for making the same.

11 Claims, 9 Drawing Sheets

TRANSGENIC CHICKEN COMPRISING AN INACTIVATED IMMUNOGLOBULIN GENE

CROSS-REFERENCING

This application is a continuation of U.S. patent application Ser. No. 14/114,159, filed on Nov. 18, 2013, which is a 371 National Phase of PCT/US2012/039191, filed on May 23, 2012, which claims the benefit of U.S. provisional application Ser. No. 61/489,638, filed May 24, 2011, all of which applications are incorporated by reference herein.

GOVERNMENT SUPPORT

This invention was made with Government support under Small Business Innovation Research contract R43 GM090626-01. The Government has certain rights in this invention.

BACKGROUND

During the past century, antibodies have been used therapeutically. Initially, therapeutic antibodies were administered as the naturally occurring polyclonal mixture from sera from immunized animals. While these products were efficacious, the serious side effects created by the anti-animal immune response of patients limited their use. Subsequently, monoclonal antibodies recovered from immunized mice were spliced onto a human constant region to produce chimeric antibodies that are approximately 70% human and 30% murine. The intensity of the anti-murine antibody response in patients treated with chimeric antibodies is significantly reduced. The ultimate goal of recovering fully human antibodies from immunized animals has been achieved by inactivating the endogenous immunoglobulin genes and substituting their human counterparts in the animal genome.

SUMMARY

Provided herein is a germline competent chicken cell comprising an endogenous heavy chain immunoglobulin locus in which at least a portion of the endogenous JH region is deleted. In particular embodiments, the JH region is replaced by a sequence that comprises a selectable marker. In some embodiments, the cell may be present in vitro. In other embodiments, the cell may be present in vivo. The cell may be a gonocyte or a primordial germ cell, for example.

Also provided herein is a chicken comprising an endogenous heavy chain immunoglobulin locus in which at least a portion of the endogenous JH region is deleted. In particular embodiments, the endogenous heavy chain immunoglobulin locus in which at least a portion of the endogenous JH region is deleted is in a germline cell of said chicken. In some cases, the chicken may be chimeric for cells that comprise said endogenous heavy chain immunoglobulin locus in which at least a portion of the endogenous JH region is deleted.

In particular embodiments, the chicken may be a transgenic chicken, and the chicken may be homozygous or heterozygous for the locus. The chicken may additionally contain an inactivated light chain locus.

In certain cases, any deleted portion of the genome may be replaced by another sequence.

Also provided are isolated nucleic acids. In one embodiment, the isolated sequence is at least 95% identical to nucleotides 1760 to 1957 of SEQ ID NO:15. In another embodiment, the isolated sequence may be at least 95% identical to nucleotides 2865-4932 of SEQ ID NO:15. In some embodiments, an isolated polynucleotide may comprise: the JH region of a chicken heavy chain immunoglobulin locus; and at least 400 bp of the sequence that flanks the 5' end of said JH region in said locus; and at least 400 bp of the sequence that flanks the 3' end of said JH region in said locus. In certain cases, the JH region may be at least 95% identical to nucleotides 2324-2380 of SEQ ID NO: 15.

A vector for inactivating the endogenous heavy chain immunoglobulin locus of a chicken genome is also provided. In certain cases, the vector may comprise: in order from 5' to 3': at least 400 bp 5' of the JH region of said heavy chain immunoglobulin locus; a selectable marker cassette; and at least 400 bp 3' of the JH region of said heavy chain immunoglobulin locus, wherein said vector does not contain said JH region. In certain cases, the vector contains the VH or C regions of said endogenous heavy chain immunoglobulin locus. In some cases, the at least 400 bp 5' of the JH region comprises a nucleotide sequence that is at least 95% identical to nucleotides 1760 to 1957 of SEQ ID NO:15. In some cases, the at least 400 bp 3' of the JH region comprises a nucleotide sequence that is at least 95% identical to nucleotides 2865-4932 of SEQ ID NO:15.

Also provided is a germline competent chicken cell comprising an endogenous light chain immunoglobulin locus in which the endogenous V-J-C region or a portion of the endogenous V-J region has been inactivated. In these embodiments, the V-J-C region may be replaced by a sequence that comprises a selectable marker. As above, the cell may be present in vitro or in vivo, and may be a gonocyte or a primordial germ cell, for example.

A chimeric chicken comprising an above-described cell in the germline of the chicken is also provided, as is a transgenic chicken comprising an endogenous light chain immunoglobulin locus in which the endogenous V-J-C region or a portion of the endogenous V-J-C has been inactivated. The chicken may be homozygous or heterozygous for said locus.

Also provided is a vector for inactivating the endogenous light chain immunoglobulin locus of a chicken genome, comprising, in order from 5' to 3': at least 400 bp 5' of the V region of said light chain immunoglobulin locus; a selectable marker cassette; and at least 400 bp 3' of the C region of said light chain immunoglobulin locus.

DEFINITIONS

Figure 1:
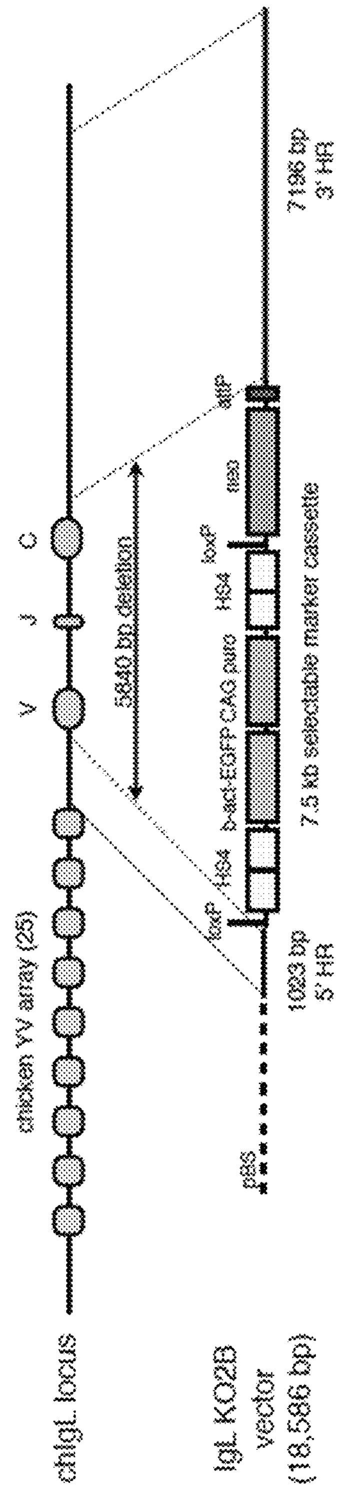
FIG. 1 schematically illustrates an IgL-VJC knockout vector.

The terms "determining", "measuring", "evaluating", "assessing" and "assaying" are used interchangeably herein to refer to any form of measurement, and include determining if an element is present or not. These terms include both quantitative and/or qualitative determinations. Assessing may be relative or absolute. "Determining the presence of" includes determining the amount of something present, as well as determining whether it is present or absent.

The term "gene" refers to a nucleic acid sequence comprised of a promoter region, a coding sequence, and a 3'UTR.

The terms "protein" and "polypeptide" are used interchangeably herein.

The term "nucleic acid" encompasses DNA, RNA, single stranded or double stranded and chemical modifications thereof. The terms "nucleic acid" and "polynucleotide" are used interchangeably herein.

The term "progeny" or "off-spring" refers to any and all future generations derived and descending from a particular animal. Thus, progeny of any successive generation are included herein such that the progeny, the F1, F2, F3, generations and so on are included in this definition.

The phrase "transgenic chicken" refers to a chicken comprising cells containing foreign nucleic acid (i.e., recombinant nucleic acid that is not native to the animal). The foreign nucleic acid may be present in all cells of the animal or in some but not all cells of the animal. The foreign nucleic acid molecule is called a "transgene" and may contain one or many genes, cDNA, etc. By inserting a transgene into a fertilized oocyte or cells from the early embryo, the resulting transgenic animal may be fully transgenic and able to transmit the foreign nucleic acid stably in its germline. Alternatively, a foreign nucleic acid may be introduced by transferring, e.g., implanting, a recombinant cell or tissue containing the same into an animal to produce a partially transgenic animal. Alternatively, a transgenic animal may be produced by transfer of a nucleus from a genetically modified somatic cell or by transfer of a genetically modified pluripotential cell such as an embryonic stem cell or a primordial germ cell.

The term "operably-linked" refers to the association of nucleic acid sequences on a single nucleic acid fragment so that the function of one is affected by the other. For example, a promoter is operably-linked with a coding sequence when it is capable of affecting the expression of that coding sequence (i.e., the coding sequence is under the transcriptional control of the promoter). Similarly, when an intron is operably-linked to a coding sequence, the intron is spliced out of the mRNA to provide for expression of the coding sequence. In the context of gene conversion, two nucleic acids sequences are operably linked if one sequence can "donate" sequence to the other by gene conversion. If two sequences are unlinked in that one can donate sequence to the other via gene conversion, the donating sequences may be upstream or downstream of the other, and the two sequences may be proximal to each other, i.e., in that there are no other intervening genes. "Unlinked" means that the associated genetic elements are not closely associated with one another and the function of one does not affect the other.

The terms "upstream" and "downstream" are used with reference to the direction of transcription.

The term "homozygous" indicates that identical alleles reside at the same loci on homologous chromosomes. In contrast, "heterozygous" indicates that different alleles reside at the same loci on homologous chromosomes. A transgenic animal may be homozygous or heterozygous for a transgene.

The term "endogenous", with reference to a gene, indicates that the gene is native to a cell, i.e., the gene is present at a particular locus in the genome of a non-modified cell. An endogenous gene may be a wild type gene present at that locus in a wild type cell (as found in nature). An endogenous gene may be a modified endogenous gene if it is present at the same locus in the genome as a wild type gene. An example of such a modified endogenous gene is a gene into which a foreign nucleic acid is inserted. An endogenous gene may be present in the nuclear genome, mitochondrial genome etc.

The term "construct" refers to a recombinant nucleic acid, generally recombinant DNA, that has been generated for the purpose of the expression of a specific nucleotide sequence (s), or is to be used in the construction of other recombinant nucleotide sequences. A construct might be present in a vector or in a genome.

The term "recombinant" refers to a polynucleotide or polypeptide that does not naturally occur in a host cell. A recombinant molecule may contain two or more naturally-occurring sequences that are linked together in a way that does not occur naturally. A recombinant cell contains a recombinant polynucleotide or polypeptide. If a cell receives a recombinant nucleic acid, the nucleic acid is "exogenous" to the cell.

The term "selectable marker" refers to a protein capable of expression in a host that allows for ease of selection of those hosts containing an introduced nucleic acid or vector. Examples of selectable markers include, but are not limited to, proteins that confer resistance to antimicrobial agents (e.g., hygromycin, bleomycin, or chloramphenicol), proteins that confer a metabolic advantage, such as a nutritional advantage on the host cell, as well as proteins that confer a functional or phenotypic advantage (e.g., cell division) on a cell.

The term "expression", as used herein, refers to the process by which a polypeptide is produced based on the nucleic acid sequence of a gene. The process includes both transcription and translation.

The term "introduced" in the context of inserting a nucleic acid sequence into a cell, means "transfection", or 'transformation" or "transduction" and includes reference to the incorporation of a nucleic acid sequence into a eukaryotic or prokaryotic cell wherein the nucleic acid sequence may be incorporated into the genome of the cell (e.g., chromosome, plasmid, plastid, or mitochondrial DNA), converted into an autonomous replicon, or transiently expressed (e.g., transfected mRNA).

The term "replacing", in the context of replacing one genetic locus with another, refers to a single step protocol or multiple step protocol.

The term "coding sequence" refers to a nucleic acid sequence that once transcribed and translated produces a protein, for example, in vivo, when placed under the control of appropriate regulatory elements. A coding sequence as used herein may have a continuous ORF or might have an ORF interrupted by the presence of introns or non-coding sequences. In this embodiment, the non-coding sequences are spliced out from the pre-mRNA to produce a mature mRNA.

As used herein the term "isolated," when used in the context of an isolated nucleic acid, refers to a nucleic acid that has been removed from its natural environment.

The term "plurality" refers to at least 2, at least 5, at least 10, at least 20, at least 50, at least 100, at least 200, at least 500, at least 1000, at least 2000, at least 5000, or at least 10,000 or at least 50,000 or more. In certain cases, a plurality includes at least 10 to 50. In other embodiments, a plurality may be at least 50 to 1,000.

As used herein, the term "germline competent chicken cell" refers to a cell that is able to contribute to the germ line of a chicken and transmit target loci to progeny. Such a cell may be present in vitro (i.e., a cultured cell) or in vivo (i.e., in a living chicken).

The terms "gene" and "locus" are used interchangeably herein. Neither term implies that a gene is actively transcribed or intact. Both terms encompass genes that have been inactivated.

The term "inactivated" is intended to indicate a gene that is not expressed in the sense that the protein encoded by the gene is not expressed. Genes can be inactivated by removing a portion of a coding sequence and/or regulator sequence of a gene. A gene that is disrupted, e.g., "knockout", is a type of inactivated gene. A locus that once contained an expressed endogenous sequence that has since been replaced by a human immunoglobulin sequence that is also expressed contains an inactivated endogenous gene. As such, a locus that contains an expressed human immunoglobulin sequence can have an inactivated endogenous immunoglobulin gene if the endogenous immunoglobulin gene was replaced by the human immunoglobulin sequence. In many case this may be done by knocking out the endogenous sequence (e.g., by deletion of at least part of the sequence) and then inserting the human immunoglobulin sequence at a position that was once occupied by the endogenous sequence.

The term "corresponding", in the context of two nucleotide sequences, is intended to indicate that the sequences are share significant sequence identity and are positioned across from one another if two sequences are aligned. For example, the JH region of one heavy chain immunoglobulin locus corresponds to the JH region of another heavy chain immunoglobulin (e.g., one from another animal) if the sequences align with one another and positioned in a similar way relative to other sequence elements.

The term "in vitro" refers to a cell that in culture, i.e., outside of an organism.

The term "in vivo" refers to a cell that is in a living organism.

As used herein, the term "gonocyte" refers to a germ cell in a differentiated gonad that is responsible for gametogenesis (i.e., spermatogenesis in males and oogenesis in females). Gonocytes include gametogonia (spermatogonia and oogonia), oocytes, ootids, and ova. The term "gonocyte" is intended to explicitly exclude primordial germ cells that are migrating and have not yet taken up residence in an undifferentiated gonad.

The term "primordial germ cell" refers to cells that, in an animal, are migrating and have not yet taken up residence in an undifferentiated gonad. Such cells may be cultured in vitro and implanted into an animal. After implantation, those cells can migrate and take up residence in the gonad.

As used herein, a "chimeric" chicken is a chicken containing a significant number of genetically distinct cells from at least two sources. A chimeric animal may be made by implanting cells from one animal into an embryo of another animal, or by implanting cultured cells (that, e.g., have a modified genome) into an embryo. The implanted cells may be harvested from a culture prior to incorporation into the host embryo. The embryo develops into an animal, and the resultant animal may contain cells from the host as well as the implanted cells. If the donated cells contain an exogenous nucleic acid (i.e., nucleic acid that is not endogenous to the cells), the progeny of the chimeric animal may be "transgenic", where a "transgenic" animal is an animal made up cells containing foreign nucleic acid (i.e., recombinant nucleic acid that is not native to the animal). The foreign nucleic acid molecule may be called a "transgene" herein.

Further definitions may be elsewhere in this disclosure.

DETAILED DESCRIPTION

Before the present subject invention is described further, it is to be understood that this invention is not limited to particular embodiments described, and as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a cell" includes a plurality of cells and reference to "a candidate agent" includes reference to one or more candidate agents and equivalents thereof known to those skilled in the art, and so forth. It is further noted that the claims may be drafted to exclude any optional element. As such, this statement is intended to serve as antecedent basis for use of such exclusive terminology as "solely", "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Germline Competent Cells

A germline competent chicken cell comprising an endogenous heavy chain immunoglobulin locus that has been inactivated is also provided. In particular embodiments, this cell may contain a knockout of the endogenous heavy chain immunoglobulin locus in which at least the JH region of the locus has been replaced by a selectable marker. Germline competent chicken cells that contain a genome in which both the endogenous heavy and light chain immunoglobulin loci have been inactivated are also provided.

A germline competent chicken cell comprising an endogenous light chain immunoglobulin locus in which the endogenous V-J-C region has been inactivated is also provided. In particular embodiments, this cell may contain a knockout of the endogenous light chain immunoglobulin locus in which the endogenous V-J-C region has been replaced by a selectable marker. Removal of the endogenous V region from the endogenous light chain immunoglobulin locus provides a locus that is not expressed in that the locus is not transcribed and no transcript is detected.

The germline competent chicken cell may be present in vitro (i.e., may be a cultured cell) or in vivo (i.e., may be in a living chicken, e.g., a chicken embryo). The cell may be, for example, a gonocyte or a primordial germ cell, both of which cell types are present in chicken embryos and can be cultured and manipulated in vitro (see, e.g., U.S. patent application Ser. No. 12/986,868, filed on Jan. 7, 2011 and references cited therein). Both gonocytes and and primordial germ cells can contribute to the germ line when implanted into a chicken embryo.

Methods for culturing primordial germ cells as well as for introducing nucleic acid into the same are well established. Examples of such methods are described in Allioli et al (Dev Biol. 1994 165:30-7), Chang et al (Cell Biol. Int. 1995 19:143-9), Chang et al, (Cell Biol. Int. 1997 21:495-9), Han et al (Mol. Reprod. Dev. 2005 72:521-9), van de Lavoir et al, (Nature 2006 441: 766-9) Shiue et al (Reprod. Domest. Anim 2009 44:55-61) and Park et al, (Biol. Reprod. 2003 68:1657-62). Cultured chicken primordial germ cells are also discussed in the following reviews: Kerr et al (Methods Enzymol. 2006 419:400-26), Petitte et al (Mech. Dev. 2004 121:1159-68) and Petitte et al (Poult Sci. 1997 76:1084-92). Methods for culturing chicken gonocytes as well as for introducing nucleic acid into the same are described in U.S. patent application Ser. No. 12/986,868, filed on Jan. 7, 2011 and in Leighton et al (Mol. Reprod. Dev. 2008 75: 1163-75).

Targeting Vectors

Vectors for inactivating the light and/or heavy chain immunoglobulin locus of a chicken genome are also provided.

In certain embodiments, the vector is for inactivating the heavy chain immunoglobulin locus of a chicken genome. In these embodiments, the vector may comprise, in order from 5' to 3': a) a sufficient length of sequence 5' of the JH region of the heavy chain immunoglobulin locus to effect homologous recombination; b) a selectable marker cassette; and c) a sufficient length of sequence 3' of the JH region of the heavy chain immunoglobulin locus to effect homologous recombination. In certain embodiments, the vector may comprise, in order from 5' to 3': a) at least 400 nt (e.g., at least 500 nt, at least 1 kb, at least 2 kb or at least 5 kb) of sequence 5' of the JH region of the heavy chain immunoglobulin locus; b) a selectable marker cassette; and c) at least 400 nt (e.g., at least 500 nt, at least 1 kb, at least 2 kb or at least 5 kb) of sequence 3' of the JH region of the heavy chain immunoglobulin locus. This vector may be designed to leave the endogenous array of V pseudogenes, the VH region, the D cluster, the J-Cmu intron, the constant regions, and the 3' untranslated region of the endogenous heavy chain locus intact, as shown in the figures. In some cases, the vector does not contain the JH region. In particular cases, vector may contain a nucleotide sequence that is at least 95% identical to nucleotides 1760 to 1957 of SEQ ID NO:15. Likewise, in some embodiments, the vector may contain a nucleotide sequence that is at least 95% identical to nucleotides 2865-4932 of SEQ ID NO:15.

In certain embodiments, the vector is for inactivating the light chain immunoglobulin locus of a chicken genome. In these embodiments, the vector may comprise, in order from 5' to 3': a) a sufficient length of sequence 5' of the V region of the light chain immunoglobulin locus to effect homologous recombination; b) a selectable marker cassette; and c) a sufficient length of sequence 3' of the C region of the light chain immunoglobulin locus to effect homologous recombination. In particular embodiments, the vector may comprise, in order from 5' to 3': a) at least 400 nt (e.g., at least 500 nt, at least 1 kb, at least 2 kb or at least 5 kb) of sequence 5' of the V region of the light chain immunoglobulin locus; b) a selectable marker cassette; and c) at least 400 nt (e.g., at least 500 nt, at least 1 kb, at least 2 kb or at least 5 kb) 3' of the C region of said light chain immunoglobulin locus. This vector may be designed to leave the endogenous array of V pseudogenes intact, and the 3' untranslated region of the endogenous light chain locus intact, as shown in FIG. 1.

In a particular embodiment, the vectors may contain: a) at least one selectable marker flanked by lox sites, b) an att site (e.g., an attP site) that is not between the lox sites and c) an optional selectable marker between the att site and the closest lox site. After the targeting vector is inserted into the locus, the part of the vector that is between the lox sites can be deleted using cre recombinase, and clones containing the deletion can be selected by the optional selectable marker.

After the part of the vector that is between the lox sites has been deleted, a human immunoglobulin sequence (containing, e.g., a human V-J or J region) can be inserted at the attP site of the construct using a suitable recombinase (e.g., a suitable bacteriophage recombinase).

As illustrated in the figures, the selectable marker cassette may contain one or more selectable markers, reporter proteins and sites for a recombinase (e.g., lox sites) that can be employed to select and identify cells as well delete sequences, as desired. The construction of targeting vectors for gene disruption is generally well known (see, e.g., Arakawa et al (Subcell Biochem. 2006 40:1-9), Winding et al (J Immunol Methods 2001 249: 1-16) and Müller (Mech Dev. 1999 82: 3-21). See also, Ausubel, et al, *Short Protocols in Molecular Biology,* 9rd ed., Wiley & Sons, 2007; Sambrook, et al., *Molecular Cloning: A Laboratory Manual*, Second Edition, (2001) Cold Spring Harbor, N.Y.).

Chimeric and Transgenic Chicken

Also provided is a chimeric chicken comprising an above-described cell in the germline of the chicken. Gonocytes may be implanted into a recipient embryo by, e.g., injection into the subgerminal cavity, injection into the germinal crescent, or by injection into the bloodstream, for example. The term “implanting” is intended to encompass direct (e.g., injection directly into a region) and indirect (e.g., systemic administration) methods by which cells are placed in a region of an embryo.

Methods for implanting germline competent cells into a recipient chicken embryo to produce a germline chimera are described in many of the references cited above and in, for example, Mozdziak et al, (Poultry Science 2006 85: 1764-1768), Naito et al, (Reproduction 2007 134: 577-584), Petitte et al (Development 1990 108:185-189) and Mozdziak et al (Dev. Dyn. 2003 226:439-445). In this method, the embryos may be cultured in a surrogate chicken eggshell, followed by a surrogate turkey eggshell, until hatching, following procedures modified from Borwornpinyo et al (*Culture of chicken embryos in surrogate eggshells* Poult. Sci. 2005 84:1477-1482). In an alternative method, chicken eggs may be pre-treated with an injection of a busulfan emulsion into the yolk of embryos after 24 h of incubation, according to the methods by Song et al (Mol. Reprod. Dev. 2005 70:438-444). After busulfan injection, the eggs may be returned to the incubators until they reach stage 17 (Hamburger, V., and H. L. Hamilton. 1951. A series of normal stages in the development of the chick embryo. J. Morphol. 88:49-67) when they are injected through the dorsal aorta with 600 to 3,500 cells. After injection, the eggshells can be sealed, and the eggs returned to the incubator and maintained until hatching. Naito et al, supra, describes a method by which gonocytes are injected into the bloodstream of a recipient animal. In a further example, embryos at 3 d of incubation may be injected with 1,000 to 2,000 gonocytes into the germinal crescent. The injected embryos may be cultured in a surrogate turkey eggshell until hatching, following the procedures of Borwornpinyo et al. (*Culture of chicken embryos in surrogate eggshells*. Poult. Sci. 2005 84:1477-1482). See also van de Lavoir et al, (Nature. 2006 441: 766-9).

The resultant embryo containing implanted cells may be incubated to produce a chimeric bird containing germ-line cells that are derived from the implanted cells. The progeny of such a chimeric chicken may be fully transgenic, although heterozygous for the genome modification. The progeny may be mated with other chickens to produce further progeny that may be heterozygous or homozygous for the genome modification. Alternative methods for making transgenic chickens are known.

A transgenic chicken comprising an inactivated heavy and/or light chain immunoglobulin locus is therefore provided. In certain embodiments, both the heavy and light chain loci of the transgenic chicken may be inactivated. The chicken may be homozygous or heterozygous for the inactivated heavy chain locus and/or the inactivated light chain locus.

In certain cases, no antibody expression is detectable using, e.g., ELISA, in a transgenic chicken that is homozygous for the inactivated heavy chain locus and/orhomozygous for the inactivated light chain locus.

Isolated Polynucleotides and Host Cells Containing the Same

Also provided herein is an isolated polynucleotide comprising the JH region of a chicken heavy chain immunoglobulin locus, as well as at least 500 bases of flanking sequence on both sides of the JH region in the chicken heavy chain immunoglobulin locus. In particular embodiments, the isolated polynucleotide may comprise: a) the JH region of the chicken heavy chain immunoglobulin locus; b) at least 500 bp (e.g., at least 600 bp, at least 700 bp, at least 800 bp, at least 900 bp, at least 1 kb, at least 1.5 kb, or at least 2 kb or more of the sequence that flanks the JH region on the 5' side of the JH region; and at least 500 bp (e.g., at least 600 bp, at least 700 bp, at least 800 bp, at least 900 bp, at least 1 kb, at least 1.5 kb, or at least 2 kb or more of the sequence that flanks the JH region on the 3' side of the JH region. In certain embodiments, the sequence of the JH region and/or the flanking sequence may be at least 85% (e.g., at least 90%, at least 95%, at least 97%, at least 98%, or at least 99% identical) to a sequence of SEQ ID NO:15, thereby accommodating sequencing errors, SNPs and other genotype-specific differences between sequences, where the JH region corresponds to nucleotides of SEQ ID NO: 15 the 2324-2380, and the flanking sequence may be defined by nucleotides 1760 to 1957 of SEQ ID NO:15 and/or nucleotides 2865-4932 of SEQ ID NO:15. The total length of the isolated polynucleotide may be up to, e.g., 10 kb or 20 kb or more, although constructs having a length that is greater than 20 kb are envisioned. The isolated polynucleotide may be contained in a non-chicken host cell, e.g., in a vector or integrated into the genome. The host cell may be of any species, including bacteria, a non-chicken bird, or yeast, etc.

Utility

The above-described chicken, particularly a transgenic chicken that has both an inactivated heavy chain gene and an inactivated light chain gene, may be employed to make fully human antibodies that have therapeutic potential. In particular embodiments, the genome of the transgenic chicken may be further modified to contain human immunoglobulin sequences (e.g., human germline sequences) so that human antibodies can be produced by the chicken. The inactivation of the endogenous heavy and light chain loci allows the expression of human immunoglobulin sequences that can be inserted into the loci without any interference from transcriptional activity and/or RNA transcribed from the endogenous loci. A deletion of only the J-C of the light chain immunoglobulin locus does not abolish transcription of the light chain immunoglobulin locus and, as such, the locus is not inactivated. The expression of human immunoglobulin sequences that are inserted downstream of such a deletion may be inhibited by this activity and/or the RNA produced thereby. In one embodiment, the chicken genome may be modified to provide for the production of antibodies that contain a synthetic V region (see e.g., US20110055938, which is incorporated by reference in its entirety, including all figures and strategies for making such antibodies, for disclosure of such methods). Methods for isolating sequences for antibodies can be produced by such a system are well known (see, e.g., US2010/0092955, which is incorporated by reference in its entirety, including all figures and strategies for making such identifying such, for disclosure of such methods,).

EXAMPLES

The following examples are provided in order to demonstrate and further illustrate certain embodiments and aspects of the present invention and are not to be construed as limiting the scope thereof.

Example 1

IgL-VJC Knockouts

In this method, the functional V region and promoter are removed in addition to the J and C regions. By removing the V region and promoter, there is no possibility of expression of the functional V in the knockout allele. Expression of the V region by itself (without J and C) would not be functional but could complicate further uses of the knockout chicken. For example, if transgenes for the expression of human antibodies are introduced into the IgL-JC knockout chicken, the remaining V region could potentially interfere with expression of the human antibodies.

A targeting vector was prepared with 1023 bp 5' homology to the promoter region of the functional chicken VL gene and 7196 bp of 3' homology to the region downstream of the C region. The vector deletes a total of 5840 bp including the V, J, C regions and 1289 bp of the V region promoter. The knockout inserts a selectable marker cassette including an EGFP gene, a puromycin resistance gene, and a promoterless neomycin resistance gene with an attP site. The selectable markers are flanked by loxP sites for later excision with Cre recombinase. The homology regions were cloned by genomic PCR from the cell line WL43 used for gene targeting experiments.

Figure 2:
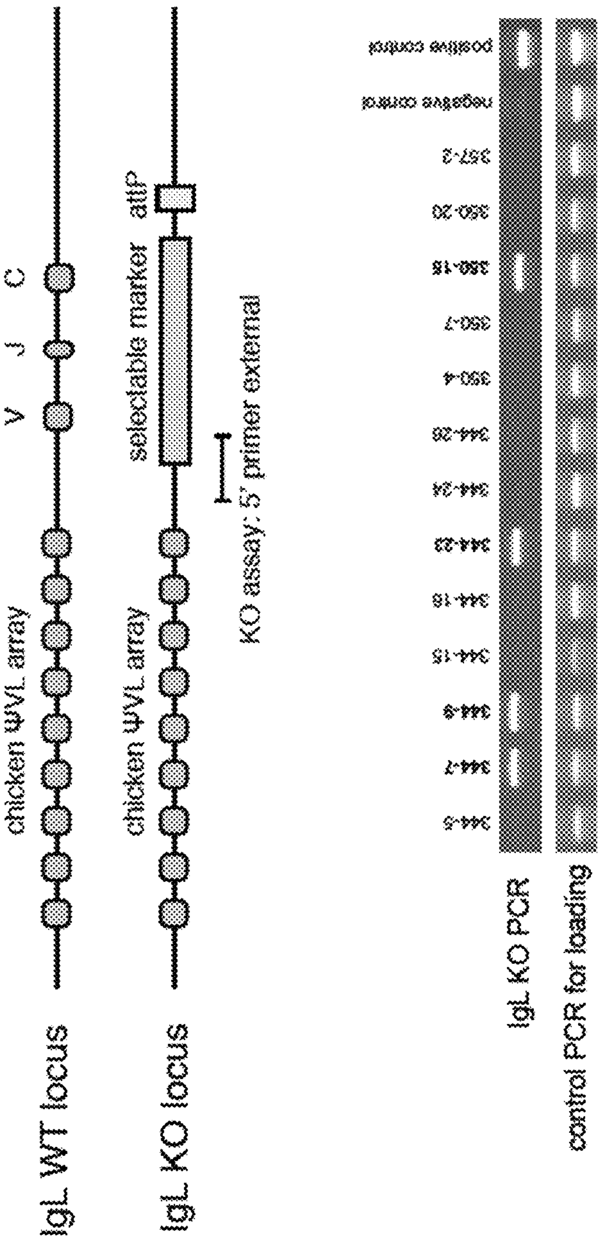
FIG. 2 illustrates the resultant IgL-VJC knockout, and is a gel showing the targeting of the light chain locus in primordial germ cells. A total of four knockout clones were found in this experiment.

The IgL knockout vector was linearized and electroporated into two PGC cell lines, WL43 and Nu69. Clones were selected with puromycin and analyzed by PCR for the knockout (FIG. 2).

TABLE 1

Frequency of targeting the light chain in PGCs. The number of targeted clones out of the total number of clones screened is shown.

| Cell line | Frequency |
|---|---|
| WL43 | 18/58 (31%) |
| Nu69 | 9/60 (15%) |

Figure 3:
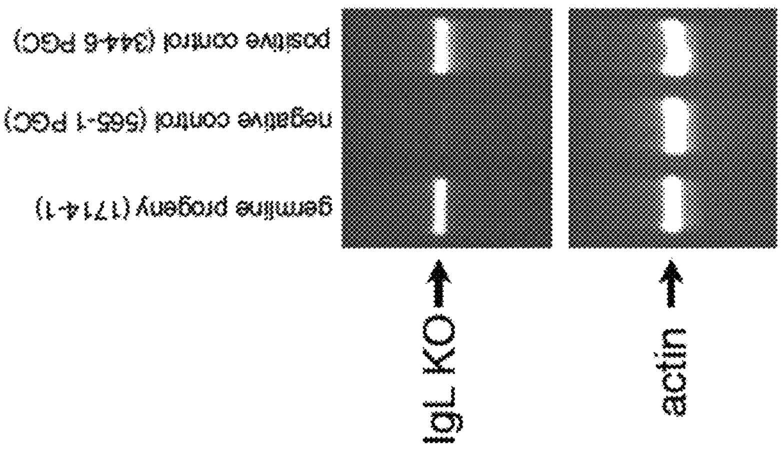
FIG. 3 shows germline transmission of IgL KO. The PCR assay shown in FIG. 2 was used to detect the IgL KO in germline progeny from chimera 1714 (cell line 438-3).

Several IgL KO clones were injected into embryos to produce germline chimeras to pass the knockout to the next generation. As shown in FIG. 3, germline transmission was obtained. The germline progeny in this case was euthanized in order to establish a newly derived gonadal cell line carrying the knockout. Germline transmission from two cell lines was obtained (438-3 and 624-3).

The primers used for the knockout assay are as follows: forward primer in chIgL 5' flanking region: 5'-actgtgctgcaggtggctatg-3' (SEQ ID NO:1); reverse primer in selectable marker cassette: 5'-atacgatgttccagattacgctt-3' (SEQ ID NO:2); control primers for loading (in chIgL locus): 5'-actgtgctgcaggtggctatg-3' (SEQ ID NO:3); and reverse primer: 5'-tcagcagcagcagtgcggac-3' (SEQ ID NO:4). The IgL KO2B sequence is shown in SEQ ID NO:5.

Example 2

IgH Knockouts

To create a null mutation in the chicken heavy chain locus, the single JH segment was deleted, which is a necessary domain in all immunoglobulins produced by the endogenous immune system.

Figure 4:
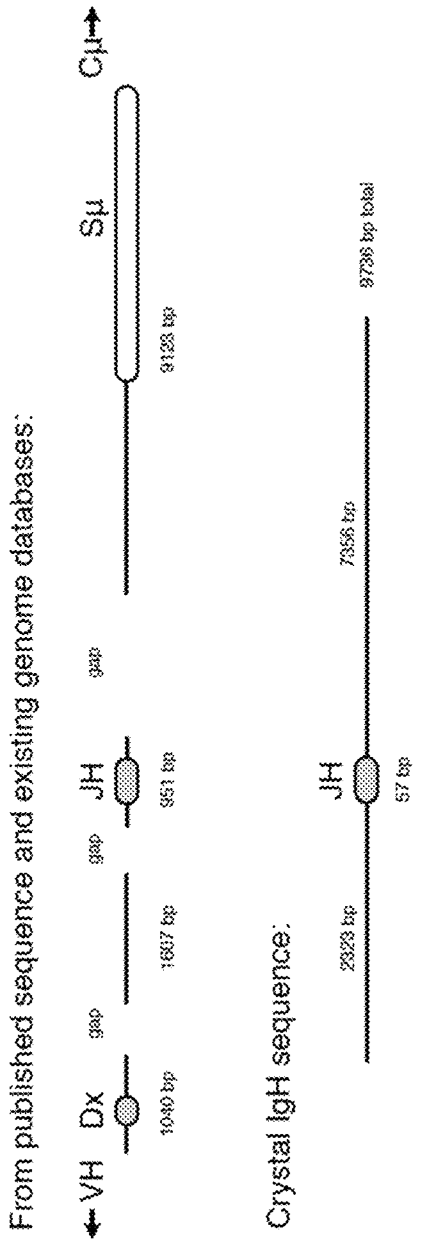
FIG. 4. illustrates sequencing of chicken genomic region surrounding single JH segment. Top line, compilation of published and genome database sequences with position of gaps indicated. The sizes of each contig are shown below the line. Bottom diagram shows Crystal's 9736 bp contig, with 2.3 kb upstream and 7.4 kb downstream of the 57 bp JH segment, extending into the Sμ region. No D sequence was identified.
Figure 5:
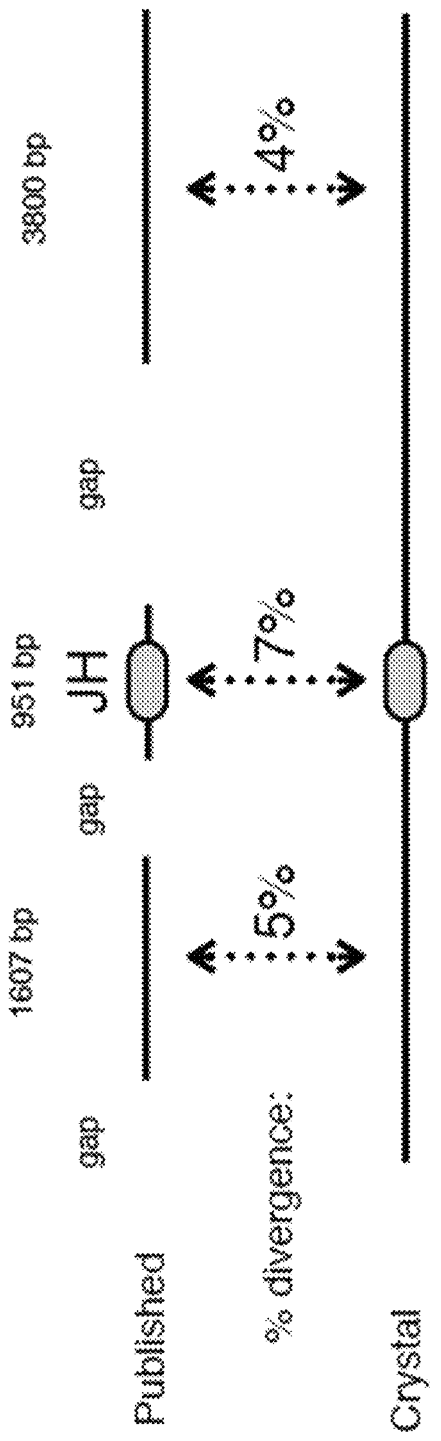
FIG. 5 schematically illustrates the sequence divergence between published genome sequences and the obtained IgH sequence.

To design a targeting vector that deletes the JH segment in chicken PGCs, it was first necessary to identify genomic flanking sequences to use as 5' and 3' homology regions. The chicken genome databases were queried, using the published JH and D sequences (Reynaud et al Cell. 1989 59:171-83) and published sequence near the Sμ switch region. Several contigs could then be assembled in silico, although gaps remained between the D, JH and switch region contigs (FIG. 4). These gaps needed to be bridged in order to build a targeting vector for the JH segment. PCR was used to amplify products across the region, spanning the gaps. PCR was performed using template genomic DNA from the PGC cell line used for targeting (Nu69, aka WL43). Alignment of these PCR product sequences produced a single long contig spanning over 9.7 kb around the JH segment, from 2.3 kb upstream to 7.4 kb downstream of the JH (FIG. 5). Comparison of these sequences to the available database sequences showed a high degree of sequence divergence (FIG. 5). The new sequence indicates that the gaps in the published sequence are predicted to be about 200 bp on the 5' side of JH and about 2 kb on the 3' side.

Figure 6:
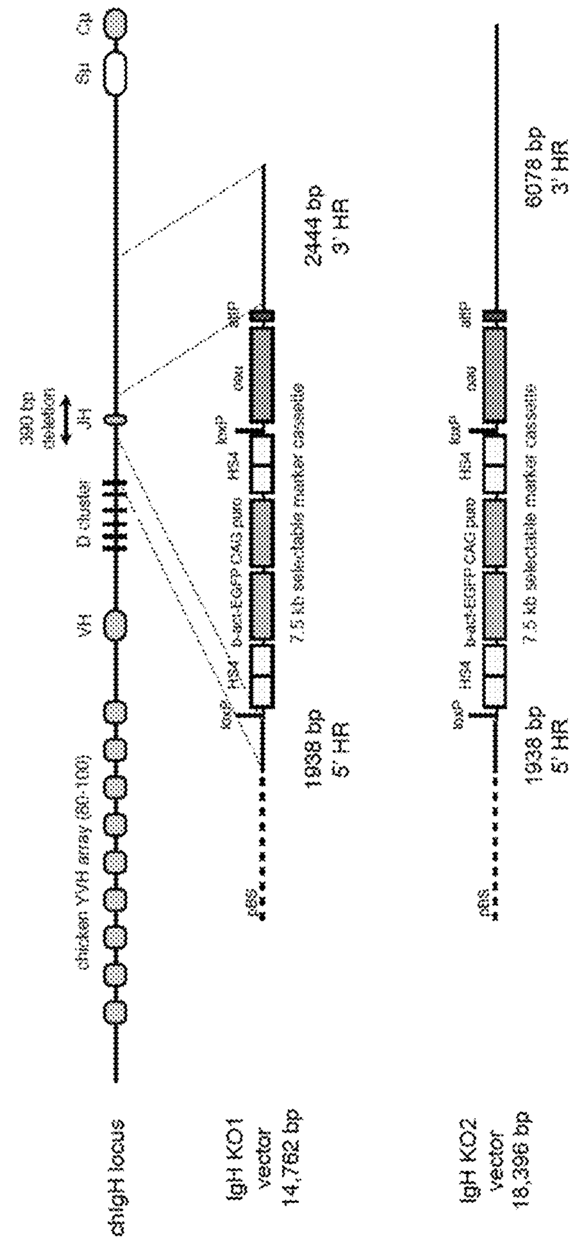
FIG. 6 schematically illustrates vectors IgH KO1 and IgH KO2 that are designed to delete the JH segment.

Using the sequences amplified from the PGC cells, two targeting vectors were prepared, identical except for varying lengths of 3' homology regions. The 5' HR in both vectors is 1938 bp, and the 3' HR is either 2444 bp (IgH KO1; FIG. 6) or 6078 bp (IgH KO2; FIG. 6). A selectable marker cassette containing the chicken β-actin promoter driving the EGFP gene, a puromycin selectable marker driven by the CAG promoter and a promoterless neo selectable marker with attP site was included. HS4 insulators from the chicken β-globin gene flank the EGFP and puro genes, and loxP sites are included for Cre-mediated excision of EGFP and puro. These vectors are designed to delete 390 bp from the chicken genome including the single JH region.

Figure 7:
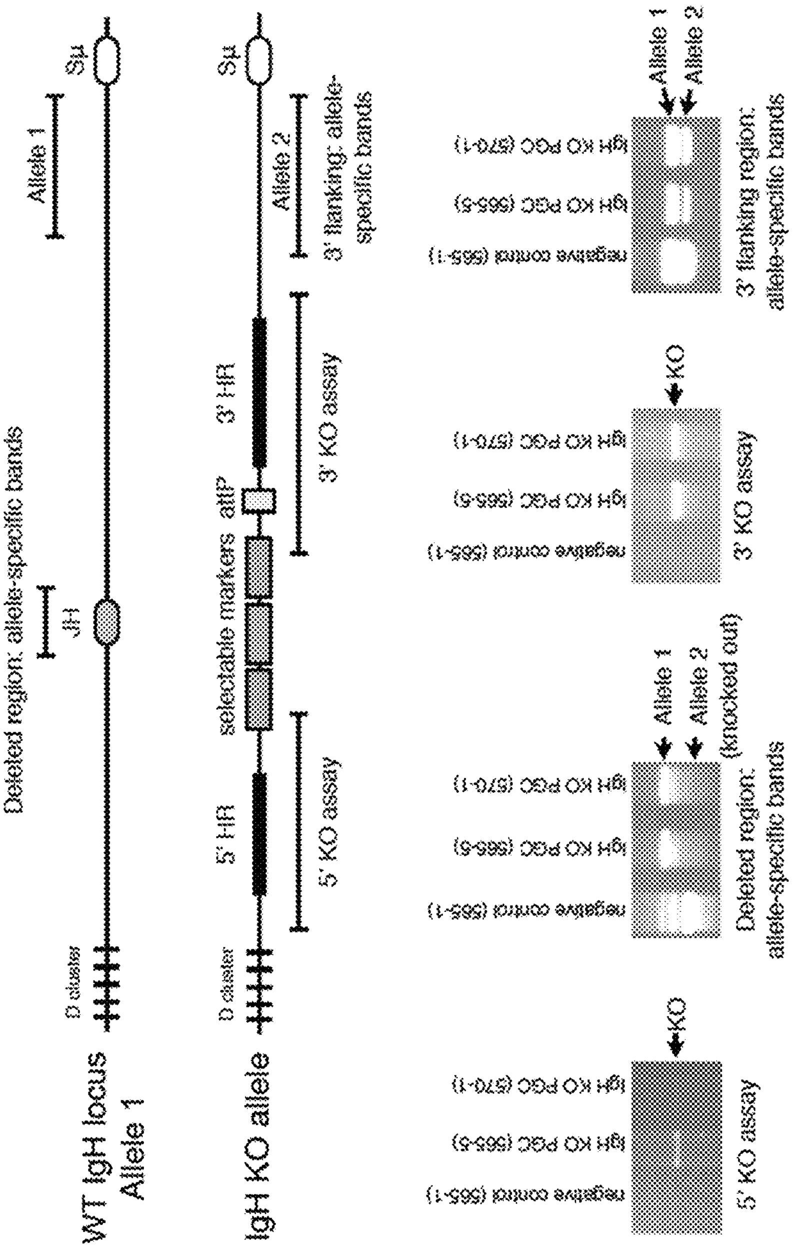
FIG. 7 shows results of a PCR analysis of targeting the JH segment in PGCs using IgH KO1. Two knockout clones and one wild type (WT) control clone are shown. Locations of the PCR products are indicated in the diagrams.

The IgH KO1 vector was linearized with NotI and electroporated into PGC cell line WL43, the source of the homology region sequences. From 8 transfections, 29 clones were isolated. Several sets of primers were used to screen the clones. Primers were used to detect the targeted insertion on both the 5' and 3' sides of insertion, where one primer hybridizes to the flanking genomic region (not present on the targeting vector) and the other primer hybridizes to the selectable marker cassette (FIG. 7). The loss of the JH region was confirmed using primers which detect different sized products from the two alleles in WL43 cells. In WL43, the two alleles show many polymorphisms, including single nucleotide polymorphisms and insertions/deletions of moderate length which can result in different sized PCR products. In the knockout cells, one of the two PCR bands, corresponding to one of the alleles, was consistently absent, indicating the knockout of that allele. The other allele consistently amplified, as expected for a heterozygous cell line. As a control, PCR was performed using primers from a nearby region of the heavy chain locus which also produce different sized products from the two alleles, to confirm that a general loss of the region (such as loss of a chromosome) had not occurred. Both alleles amplified from this flanking region, indicating presence of both alleles in regions of the heavy chain that should not be affected by the knockout of the JH region.

The 5' KO assay product was sequenced and showed the expected sequence for the knockout. FIG. 7 shows the analysis of two clones using all four PCR assays. For the majority of clones, only the 5' assay and the deleted region assay were performed.

Figure 8:
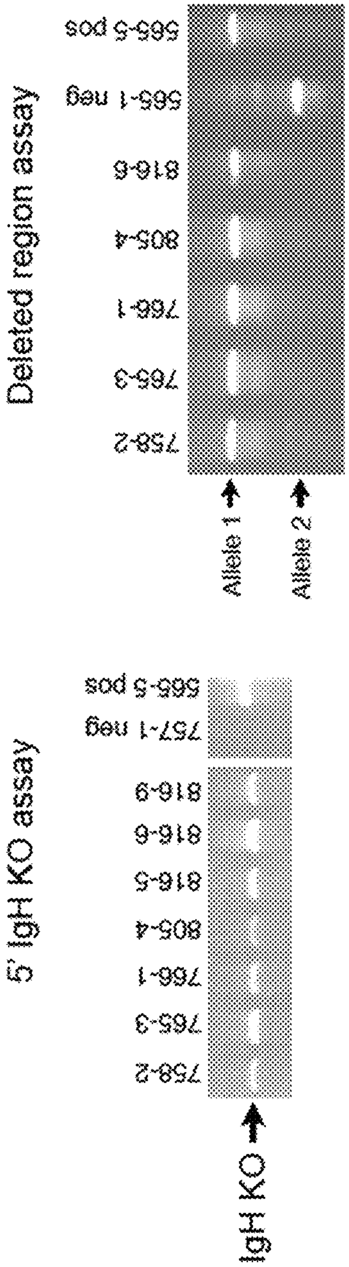
FIG. 8 shows the results of PCR analysis of targeting the JH segment using the IgH KO2 vector. Analysis of a subset of the clones is shown. The 5' IgH KO assay and Deleted region assays both indicated the correct targeting event.

The IgH KO2 vector was linearized with NotI and electroporated into PGC cell line WL43 (aka Nu69). From 41 transfections, a total of 81 stable transfected clones were obtained. Of these clones, 59 were expanded for analysis of gene targeting, and targeting was observed in 15 clones, for a frequency of approximately 25%. The clones were analyzed by PCR for the 5' assay and deleted region assay (FIG. 8). No 3' KO assay was performed owing to the much longer 3' homology region in this vector.

PGC clones carrying the IgH KO were injected into embryos at day 3 of incubation in order to produce chimeric chickens with the knockout PGCs in the germline. These embryos contained a mixture of PGCs of their own plus the injected cells carrying the chicken heavy chain knockout. The embryos were incubated, the chicks were hatched and animals were grown to sexual maturity. These birds are referred to as the G0 generation. To pass the genetic modification on to the the next generation, the germline chimeras were bred to normal, wild type chickens and progeny were tested for those that inherit the modification. The heavy chain knockout allele contains the gene encoding green fluorescent protein (GFP) that causes the birds to glow green under illumination with a handheld UV lamp, allowing us to screen quickly for germline transmission. These birds are called heterozygotes of the G1 generation, for they are the first generation to carry the genetic modification in all cells of the body, not just the germline. These G1 birds are then bred to wild type chickens to propagate the line, or heterozygotes are mated to each other to produce homozygous animals.

Figure 9:
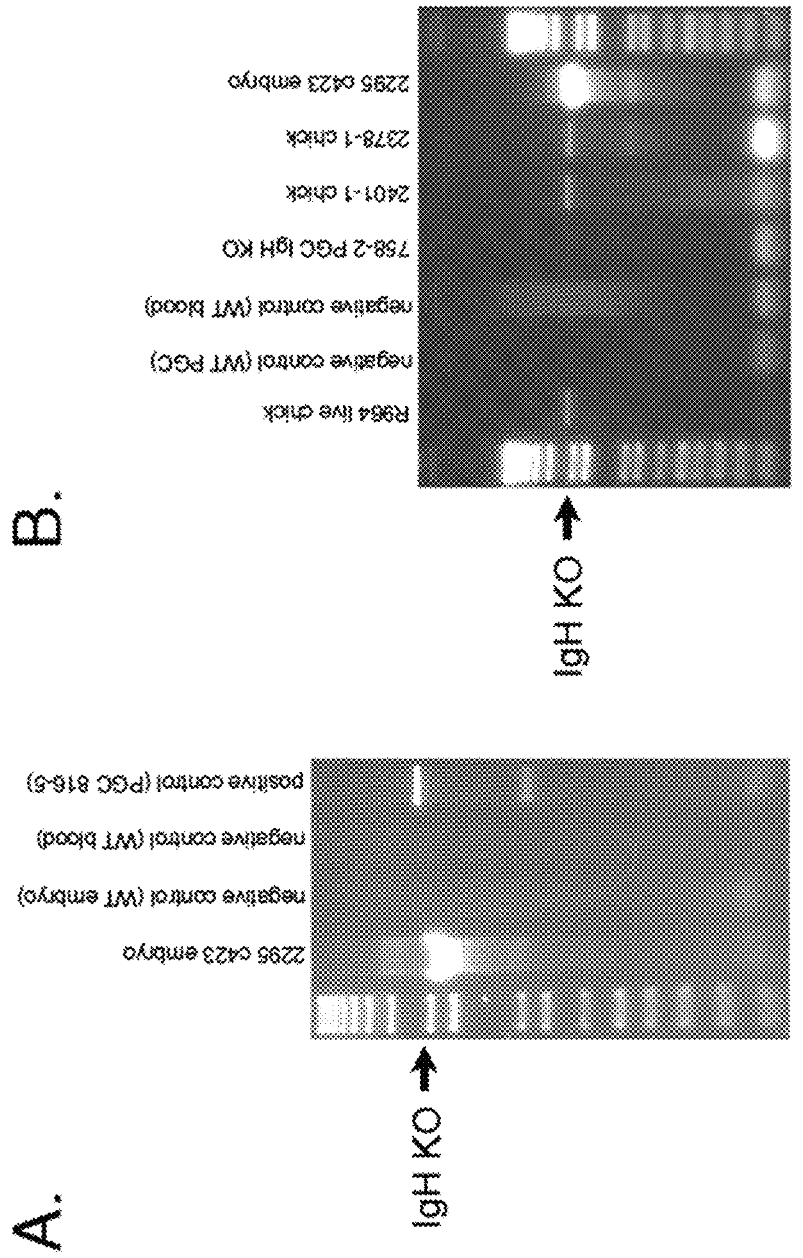
FIG. 9 panel A shows the results of a PCR analysis using the 5' KO assay for the IgH KO was performed on a GFP-positive embryo obtained from breeding chimera 2295. A very strong amplification was obtained from the embryo relative to the positive control (an IgH KO PGC line), probably owing to increased amount of genomic DNA in the sample. Wild type genomic DNA served as negative controls. Panel B. A live chick, R964, is shown to carry the IgH KO. PCR for the IgH KO was performed on comb biopsy DNA. Germline transmission in two other chicks was also observed (2401-1 and 2378-1) although these chicks did not survive.

For the heavy chain knockout, several chimeric G0 birds have produced germline progeny in which the knockout was transmitted to the next generation. Presence of the knockout in live birds was confirmed by PCR using the 5' KO assay (FIG. 9). The cell lines 758-2 and 805-4 (FIG. 8) have produced germline progeny.

The primers used in the PCR assays are as follows:

```
5' KO assay:
chDJ-F1
                                   (SEQ ID NO: 6)
CAGTGTCCAAATTCCTTAAATTTCC;

HA-R
                                   (SEQ ID NO: 7)
ATACGATGTTCCAGATTACGCTT

Deleted region
chDJ-F7
                                   (SEQ ID NO: 8)
TGAACCCATAAAGTGAAATCCTC

chJH-R3
                                   (SEQ ID NO: 9)
TTCGGTCCCGTGGCCCCAT

3' KO assay
neo-R4
                                  (SEQ ID NO: 10)
GGAACACGGCGGCATCAGAGCA

chJC-R6a2
                                  (SEQ ID NO: 11)
CCGGAAAGCAAAATTTGGGGGCAA

3' flanking region
chJC-F10
                                  (SEQ ID NO: 12)
GGGGGTTCGGTGCAGTTTTTC

chJC-R14
                                  (SEQ ID NO: 13)
ATATTGGCCCCATTTCCCCTCAG
```

The sequence of the IgH KO and KO2 vectors are set forth as SEQ ID NOS:14 and 16, respectively. The sequence of 9736 bp of the chicken IgH locus surrounding the JH segment is set forth as SEQ ID NO:15. The JH segment is represented by nucleotides 2324-2380 of this sequence. The newly identified sequence 5' of the JH segment is defined by nucleotides 1760 to 1957 of SEQ ID NO:15. The newly identified sequence 3' of the JH segment is defined by nucleotides 2865 to 4932 of SEQ ID NO:15.

What is claimed is:

1. A chicken primordial germ cell having a genome in which the endogenous heavy chain immunoglobulin locus has been modified by homologous recombination to contain a selectable marker in place of the endogenous JH region of the locus, wherein the sequences that flank the selectable marker in the modified heavy chain immunoglobulin locus are the same as or amplified from the chicken primordial germ cell prior to modification.

2. The chicken primordial germ cell of claim 1, wherein the V pseudogenes, the VH region, the D cluster, the J-C intron, the constant region, and the 3' untranslated region of the modified heavy chain immunoglobulin locus are the same as or amplified from the chicken primordial germ cell prior to modification.

3. The chicken primordial germ cell of claim 1, wherein the selectable marker is flanked by one or more lox sites.

4. The chicken primordial germ cell of claim 1, wherein the selectable marker is flanked by an attP site.

5. The chicken primordial germ cell of claim 1, wherein the selectable marker confers resistance to an antimicrobial agent.

6. The chicken primordial germ cell of claim 1, wherein the selectable marker is a puromycin or neomycin resistance gene.

7. The chicken primordial germ cell of claim 1, wherein the selectable marker is a green fluorescent protein (GFP).

8. The chicken primordial germ cell of claim 1, wherein the modified heavy chain immunoglobulin locus comprises a 5' flanking sequence that is at least 95% identical to nucleotides 1760 to 1957 of SEQ ID NO:15.

9. The chicken primordial germ cell of claim 1, wherein the modified heavy chain immunoglobulin locus comprises a 3' flanking sequence that is at least 95% identical to nucleotides 2865-4932 of SEQ ID NO:15.

10. The chicken primordial germ cell of claim 1, wherein said cell is present in vitro.

11. The chicken primordial germ cell of claim 1, wherein said cell is present in vivo.

* * * * *

SEQUENCE LISTING

```
<160> NUMBER OF SEQ ID NOS: 16

<210> SEQ ID NO 1
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 1

actgtgctgc aggtggctat g                                    21


<210> SEQ ID NO 2
<211> LENGTH: 23
<212> TYPE: DNA
<213> ORGANISM: Artificial sequence
<220> FEATURE:
<223> OTHER INFORMATION: Synthetic oligonucleotide
```

-continued

<400> SEQUENCE: 2
atacgatgtt ccagattacg ctt 23

<210> SEQ ID NO 3
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 3
actgtgctgc aggtggctat g 21

<210> SEQ ID NO 4
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 4
tcagcagcag cagtgcggac 20

<210> SEQ ID NO 5
<211> LENGTH: 18586
<212> TYPE: DNA
<213> ORGANISM: Artificial sequence
<220> FEATURE:
<223> OTHER INFORMATION: Synthetic plasmid construct

<400> SEQUENCE: 5
ctaaattgta agcgttaata ttttgttaaa attcgcgtta aatttttgtt aaatcagctc 60 atttttaac caataggccg aaatcggcaa aatcccttat aaatcaaaag aatagaccga 120
gatagggttg agtgttgttc cagtttggaa caagagtcca ctattaaaga acgtggactc 180
caacgtcaaa gggcgaaaaa ccgtctatca gggcgatggc ccactacgtg aaccatcacc 240
ctaatcaagt tttttggggt cgaggtgccg taaagcacta aatcggaacc ctaaagggag 300
cccccgattt agagcttgac ggggaaagcc ggcgaacgtg gcgagaaagg aagggaagaa 360
agcgaaagga gcgggcgcta gggcgctggc aagtgtagcg gtcacgctgc gcgtaaccac 420
cacacccgcc gcgcttaatg cgccgctaca gggcgcgtcc cattcgccat tcaggctgcg 480
caactgttgg gaagggcgat cggtgcgggc ctcttcgcta ttacgccagc tggcgaaagg 540
gggatgtgct gcaaggcgat taagttgggt aacgccaggg ttttcccagt cacgacgttg 600
taaaacgacg gccagtgagc gcgcgtaata cgactcacta tagggcgaat tgggtaccgg 660
cgcgcccatc actcagggag gagatggtcc cagcagcctt gtccctgccc tgcactgcac 720
ttagctcctg gaccccatct cctgctgccc acccatattg cctccctgtg ttgctgttgc 780
agggttgctt ctgcctcata ctggtttctc ccttctggag gtggccaaaa gccgggccct 840
gtgcaatcct ggtgcataaa taccttatgg cccctaagta gggcaggtgt gggacacgct 900
ctggcacctg ggtgtgtgc aagtgctcag gaagacctgc aggcacaggt ggcagtgggg 960
ggtctctggc tgtgctcgag cagcagctgc ctggggtaag ggtagtactc tgtgcatgaa 1020
caatgctgca gggctcagct ctgctcagac cacgaccctg gcaccaacag agacctgcct 1080
ggctctgtgg tcatgtaaac ctttacagga gctcaagaca aggctgttta ttactgctct 1140
ggcaggaaag aagcactggc catggtcata gagagttcca gcaacaggaa agtgagagcc 1200
caagctgctg aggtaccagg gctcctcagg tgcctgctgc agcagcttgg acacagtcga 1260

-continued

```
ggaacagcaa ttgtacctgt gtggtggatc aggctgtgct gcctgtgaac ctattctagc   1320
acatctgtca cctctgtgcc actcacaggg ataccacccc tgagacccct accccatcag   1380
cctctgtgtg ggatatggtg ttgggcccaa gggctctgtt gcacagggag atagaggcct   1440
ggggaggagg gaaagcattg aggtggtgtt gataccaggg atgtgagccc aagcaagaga   1500
tcagcagagc aaggaggaag aattgcaggt gttggggctg gggaaagccc cagatggctg   1560
gagctggtgg ggccactgga gatctcctcc tcccatcctg ctccatgctg gggcagctgc   1620
tgcaggctga ccagggcctg cccgggcacg ttgtgaaggt caccaaggat ggagacttca   1680
gagctagcat aacttcgtat agcatacatt atacgaagtt ataagcgtaa tctggaacat   1740
cgtatgtacc ggatccgaag caggctttcc tggaaggtcc tggaaggggg cgtccgcggg   1800
agctcacggg gacagccccc ccccaaagcc cccagggatg taattacgtc cctcccccgc   1860
tagggggcag cagcgagccg cccggggctc cgctccggtc cggcgctccc cccgcatccc   1920
cgagccggca gcgtgcgggg acagcccggg cacggggaag gtggcacggg atcgctttcc   1980
tctgaacgct tctcgctgct ctttgagcct gcagacacct gggggggatac ggggaaaaag   2040
ctttaggctg agaagcaggc tttcctggaa ggtcctggaa gggggcgtcc gcgggagctc   2100
acggggacag cccccccccca aagcccccag ggatgtaatt acgtccctcc cccgctaggg   2160
ggcagcagcg agccgcccgg ggctccgctc cggtccggcg ctccccccgc atccccgagc   2220
cggcagcgtg cggggacagc ccgggcacgg ggaaggtggc acgggatcgc tttcctctga   2280
acgcttctcg ctgctctttg agcctgcaga cacctggggg gatacgggga aaaagcttta   2340
ggctgaacta gctagtctcg aggtcgaggt gagccccacg ttctgcttca ctctccccat   2400
ctcccccccc tccccacccc caattttgta tttatttatt ttttaattat tttgtgcagc   2460
gatgggggcg gggggggggg gggcgcgcgc caggcggggc ggggcggggc gaggggcggg   2520
gcggggcgag gcggagaggt gcggcggcag ccaatcagag cggcgcgctc cgaaagtttc   2580
cttttatggc gaggcggcgg cggcggcggc cctataaaaa gcgaagcgcg cggcgggcgg   2640
gagtcgctgc gttgccttcg ccccgtgccc cgctccgcgc cgcctcgcgc cgcccgcccc   2700
ggctctgact gaccgcgtta ctcccacagg tgagcgggcg ggacggccct tctcctccgg   2760
gctgtaatta gcgcttggtt taatgacggc tcgtttcttt tctgtggctg cgtgaaagcc   2820
ttaaagggct ccgggagggc cctttgtgcg ggggggagcg gctcgggggg tgcgtgcgtg   2880
tgtgtgtgcg tggggagcgc cgcgtgcggc ccgcgctgcc cggcggctgt gagcgctgcg   2940
ggcgcggcgc ggggctttgt gcgctccgcg tgtgcgcgag gggagcgcgg ccgggggcgg   3000
tgccccgcgg tgcggggggg ctgcgagggg aacaaaggct gcgtgcgggg tgtgtgcgtg   3060
ggggggtgag caggggtgt gggcgcggcg gtcgggctgt aacccccccc tgcacccccc   3120
tccccgagtt gctgagcacg gcccggcttc gggtgcgggg ctccgtgcgg ggcgtggcgc   3180
ggggctcgcc gtgccgggcg gggggtggcg gcaggtgggg gtgccgggcg gggcggggcc   3240
gcctcgggcc ggggagggct cgggggaggg gcgcggcggc ccccggagcgc cggcggctgt   3300
cgaggcgcgg cgagccgcag ccattgcctt ttatggtaat cgtgcgagag ggcgcaggga   3360
cttcctttgt cccaaatctg gcggagccga aatctgggag gcgccgccgc acccccctcta   3420
gcgggcgcgg gcgaagcggt gcggcgccgg caggaaggaa atgggcgggg agggccttcg   3480
tgcgtcgccg cgccgccgtc cccttctcca tctccagcct cggggctgcc gcagggggac   3540
ggctgccttc gggggggacg gggcagggcg gggttcggct tctggcgtgt gaccggcggc   3600
```

-continued

```
tctagagcct ctgctaacca tgttcatgcc ttcttctttt tcctacagct cctgggcaac   3660
gtgctggttg ttgtgctgtc tcatcatttt ggcaaagaat tatcgcatgc ctgcgtcgac   3720
ggtaccgcgg gcccgggatc caccggtcgc caccatggtg agcaagggcg aggagctgtt   3780
caccggggtg gtgcccatcc tggtcgagct ggacggcgac gtaaacggcc acaagttcag   3840
cgtgtccggc gagggcgagg gcgatgccac ctacggcaag ctgaccctga agttcatctg   3900
caccaccggc aagctgcccg tgccctggcc caccctcgtg accaccctga cctacggcgt   3960
gcagtgcttc agccgctacc ccgaccacat gaagcagcac gacttcttca agtccgccat   4020
gcccgaaggc tacgtccagg agcgcaccat cttcttcaag gacgacggca actacaagac   4080
ccgcgccgag gtgaagttcg agggcgacac cctggtgaac cgcatcgagc tgaagggcat   4140
cgacttcaag gaggacggca acatcctggg gcacaagctg gagtacaact acaacagcca   4200
caacgtctat atcatggccg acaagcagaa gaacggcatc aaggtgaact tcaagatccg   4260
ccacaacatc gaggacggca gcgtgcagct cgccgaccac taccagcaga acacccccat   4320
cggcgacggc cccgtgctgc tgcccgacaa ccactacctg agcacccagt ccgccctgag   4380
caaagacccc aacgagaagc gcgatcacat ggtcctgctg gagttcgtga ccgccgccgg   4440
gatcactctc ggcatggacg agctgtacaa gtaaagcggc cggccgcgac tctagatcat   4500
aatcagccat accacatttg tagaggtttt acttgcttta aaaaacctcc cacacctccc   4560
cctgaacctg aaacataaaa tgaatgcaat tgttgttgtt aacttgttta ttgcagctta   4620
taatggttac aaataaagca atagcatcac aaatttcaca aataaagcat ttttttcact   4680
gcattctagt tgtggtttgt ccaaactcat caatgtatct taaggaaccc cttcctcgac   4740
attgattatt gactagctag ttattaatag taatcaatta cggggtcatt agttcatagc   4800
ccatatatgg agttccgcgt tacataactt acggtaaatg gcccgcctgg ctgaccgccc   4860
aacgaccccc gcccattgac gtcaataatg acgtatgttc ccatagtaac gccaataggg   4920
actttccatt gacgtcaatg ggtggactat ttacggtaaa ctgcccactt ggcagtacat   4980
caagtgtatc atatgccaag tacgccccct attgacgtca atgacggtaa atggcccgcc   5040
tggcattatg cccagtacat gaccttatgg gactttccta cttggcagta catctacgta   5100
ttagtcatcg ctattaccat gggtcgaggt gagccccacg ttctgcttca ctctccccat   5160
ctcccccccc tccccacccc caattttgta tttatttatt ttttaattat tttgtgcagc   5220
gatgggggcg gggggggggg gggcgcgcgc caggcggggc ggggcggggc gaggggcggg   5280
gcggggcgag gcggagaggt gcggcggcag ccaatcagag cggcgcgctc cgaaagtttc   5340
cttttatggc gaggcggcgg cggcggcggc cctataaaaa gcgaagcgcg cggcgggcgg   5400
gagtcgctgc gttgccttcg ccccgtgccc cgctccgcgc cgcctcgcgc cgcccgcccc   5460
ggctctgact gaccgcgtta ctcccacagg tgagcgggcg ggacggccct tctcctccgg   5520
gctgtaatta gcgcttggtt taatgacggc tcgtttcttt tctgtggctg cgtgaaagcc   5580
ttaaagggct ccgggagggc cctttgtgcg gggggggagcg gctcgggggg tgcgtgcgtg   5640
tgtgtgtgcg tggggagcgc cgcgtgcggc ccgcgctgcc cggcggctgt gagcgctgcg   5700
ggcgcggcgc ggggctttgt gcgctccgcg tgtgcgcgag gggagcgcgg ccgggggcgg   5760
tgccccgcgg tgcggggggg ctgcgagggg aacaaaggct gcgtgcgggg tgtgtgcgtg   5820
ggggggtgag cagggggtgt gggcgcggcg gtcgggctgt aacccccccc tgcacccccc   5880
tccccgagtt gctgagcacg gcccggcttc gggtgcgggg ctccgtgcgg ggcgtggcgc   5940
ggggctcgcc gtgccgggcg gggggtggcg gcaggtgggg gtgccgggcg gggcggggcc   6000
```

-continued

```
gcctcgggcc ggggagggct cgggggaggg gcgcggcggc cccggagcgc cggcggctgt   6060
cgaggcgcgg cgagccgcag ccattgcctt ttatggtaat cgtgcgagag ggcgcaggga   6120
cttcctttgt cccaaatctg gcggagccga aatctgggag gcgccgccgc accccctcta   6180
gcgggcgcgg gcgaagcggt gcggcgccgg caggaaggaa atgggcgggg agggccttcg   6240
tgcgtcgccg cgccgccgtc cccttctcca tctccagcct cggggctgcc gcagggggac   6300
ggctgccttc gggggggacg gggcagggcg gggttcggct tctggcgtgt gaccggcggc   6360
tctagagcct ctgctaacca tgttcatgcc ttcttctttt tcctacagct cctgggcaac   6420
gtgctggtta ttgtgctgtc tcatcatttt ggcaaagaat tcctagcgcc accatgaccg   6480
agtacaagcc taccgtgcgc ctggccactc gcgatgatgt gccccgcgcc gtccgcactc   6540
tggccgccgc tttcgccgac taccccgcta cccggcacac cgtggacccc gaccggcaca   6600
tcgagcgtgt gacagagttg caggagctgt tcctgacccg cgtcgggctg gacatcggca   6660
aggtgtgggt agccgacgac ggcgcggccg tggccgtgtg gactaccccc gagagcgttg   6720
aggccggcgc cgtgttcgcc gagatcggcc cccgaatggc cgagctgagc ggcagccgcc   6780
tggccgccca gcagcaaatg gagggcctgc ttgcccccca tcgtcccaag gagcctgcct   6840
ggtttctggc cactgtagga gtgagccccg accaccaggg caagggcttg ggcagcgccg   6900
tcgtgttgcc cggcgtagag gccgccgaac gcgccggtgt gcccgccttt ctcgaaacaa   6960
gcgcaccaag aaaccttcca ttctacgagc gcctgggctt caccgtgacc gccgatgtcg   7020
aggtgcccga gggacctagg acctggtgta tgacacgaaa acctggcgcc taatgatcta   7080
gaaccggtca tggccgcaat aaaatatctt tattttcatt acatctgtgt gttggttttt   7140
tgtgtgttcg aacctgcagc ccgggggatc cgaagcaggc tttcctggaa ggtcctggaa   7200
gggggcgtcc gcgggagctc acggggacag cccccccccca aagcccccag ggatgtaatt   7260
acgtccctcc cccgctaggg ggcagcagcg agccgcccgg ggctccgctc cggtccggcg   7320
ctccccccgc atccccgagc cggcagcgtg cggggacagc ccgggcacgg ggaaggtggc   7380
acgggatcgc tttcctctga acgcttctcg ctgctctttg agcctgcaga cacctggggg   7440
gatacgggga aaaagcttta ggctgagaag caggctttcc tggaaggtcc tggaaggggg   7500
cgtccgcggg agctcacggg gacagccccc ccccaaagcc cccagggatg taattacgtc   7560
cctcccccgc tagggggcag cagcgagccg cccggggctc cgctccggtc cggcgctccc   7620
cccgcatccc cgagccggca gcgtgcgggg acagcccggg cacggggaag gtggcacggg   7680
atcgctttcc tctgaacgct tctcgctgct ctttgagcct gcagacacct gggggggatac   7740
ggggaaaaag ctttaggctg aactagaatg catataactt cgtatagcat acattatacg   7800
aagttatgga tcccccaaat caatctaaag tatatatgag taacctgagg ctatggcagg   7860
gcctgccgcc ccgacgttgg ctgcgagccc tgggccttca cccgaacttg gggggtgggg   7920
tggggaaaag gaagaaacgc gggcgtattg gccccaatgg ggtctcggtg gggtatcgac   7980
agagtgccag ccctgggacc gaaccccgcg tttatgaaca aacgacccaa caccgtgcgt   8040
tttattctgt ctttttattg ccgtcatagc gcgggttcct tccggtattg tctccttccg   8100
tgtttcagtt agcctccccc tagggtgggc gaagaactcc agcatgagat ccccgcgctg   8160
gaggatcatc cagccggcgt cccggaaaac gattccgaag cccaaccttt catagaaggc   8220
ggcggtggaa tcgaaatctc gtgatggcag gttgggcgtc gcttggtcgg tcatttcgaa   8280
ccccagagtc ccgctcagaa gaactcgtca agaaggcgat agaaggcgat gcgctgcgaa   8340
```

-continued

```
tcgggagcgg cgataccgta aagcacgagg aagcggtcag cccattcgcc gccaagctct   8400
tcagcaatat cacgggtagc caacgctatg tcctgatagc ggtccgccac acccagccgg   8460
ccacagtcga tgaatccaga aaagcggcca ttttccacca tgatattcgg caagcaggca   8520
tcgccatggg tcacgacgag atcctcgccg tcgggcatgc tcgccttgag cctggcgaac   8580
agttcggctg gcgcgagccc ctgatgctct tcgtccagat catcctgatc gacaagaccg   8640
gcttccatcc gagtacgtgc tcgctcgatg cgatgtttcg cttggtggtc gaatgggcag   8700
gtagccggat caagcgtatg cagccgccgc attgcatcag ccatgatgga tactttctcg   8760
gcaggagcaa ggtgagatga caggagatcc tgccccggca cttcgcccaa tagcagccag   8820
tcccttcccg cttcagtgac aacgtcgagc acagctgcgc aaggaacgcc cgtcgtggcc   8880
agccacgata gccgcgctgc ctcgtcttgc agttcattca gggcaccgga caggtcggtc   8940
ttgacaaaaa gaaccgggcg cccctgcgct gacagccgga acacggcggc atcagagcag   9000
ccgattgtct gttgtgccca gtcatagccg aatagcctct ccacccaagc ggccggagaa   9060
cctgcgtgca atccatcttg ttcaatcatg cgaaacgatc ctcatcctgt ctcttgatcg   9120
attacgcccc caactgagag aactcaaagg ttaccccagt tggggcacac tagtgctgac   9180
tctgcatcca tgtctctgtg tcctttgcg tgctgtctgc atctcacaca gtggggtcag    9240
ccccagtatg gggaagggct ggggggcgca tacacacata ttggtaatgt tgggggcggg   9300
gggggggtgg gggggtcaac agatcagcac tggagacact ggtgtatacc ctggcaccac   9360
caacatctaa ggcagggtgc tttggggcaa ttttggggca gtttaaggtc tgtgctggca   9420
ctgagcacgt ggctgtggcc gtgctgtcct catctcccac ccactacggt ctgtgcgcca   9480
ggtccctagc agagatttgc tttatgctgg gaacaggggg agttctgggt ctgtttcctt   9540
gcattcagac accctggtgc cccctgggtg ggatgtcagt gtgaatactc ctttgtgccc   9600
tgtgcctgca gcagcctgac cctccacaca ccacacgcct tgtgtgcacc ccacccctgt   9660
cactatccct ctccccgctc cccagggaga ttttgcagtg gcccctgtag ggcagctttt   9720
agcacagccc ccagcagcaa gcaagcagaa agcactgctg tgcacagctt gtcagctgtg   9780
tgtgtttgct gaggaggatc tgtcttttgc tgaggccatc agtcttgtcc tgctcaacct   9840
ccatcgatgc tgcccacctc aacacatcta cccatctatt ccatctacac caacatctcc   9900
attcatccca cccacccaaa catgtccatc catcacaaca cctccatcca acccgcacac   9960
tccagcacct ccaatcattc catctacacc accatgctga tctgctacag ccactccaac  10020
gcaaccgtcc attccatcta caccaatgtc catccatccc agccactcca gcacctccag  10080
ccatcccacc caccctatgt ctccatccag ccactggtgg ggtgcaggac atggggccag  10140
ctctactgtc aggactgggg tttttgcatg gccccatacc acttctgcag aagagacgca  10200
ctgaaagttt ggctgaccat tttctccgcg gtagagttgt ggcagttctg taatttaggg  10260
tcttttatcc agtttggaga tgggctggga tctcccagct ccatggcagg cattcatgac  10320
actgggttta gtatctgatg ggtgggatgt ggctgaactt cattttcttt ccccagtgac  10380
aaagtttttg cagttgaata tgaattcctg ctttctgctc tatgagttgt tttttcccca  10440
ggacgtacac agggaatcag cagtcttcat tctccctctg ccatgtgtag actctgccac  10500
acaggactgt gctgtcctca tgcccctgcg cccaaattgt tgccctctgc ccatgcctgc  10560
caagctgagc ccccctgca ggctgccatg ctggattgac atgagccctg agattggtac   10620
agaaatggtg attttggggt tttctctgca ctcaggaagc tgaaggctca atgctcagtg  10680
atggatttac caaactgtgc cctgaggcag ctgctcatgc tggataaagt cactggagca  10740
```

-continued

```
caggtaacca ggcgctgggc agggatttct catgggcccc acttggaaag ctgcaggctg  10800
caagcctgga cgcctctgcc ttcacgcctc accctcatga ggacaacctc actaattatt  10860
gattaaaaga ttttgctaaa ccatctccag aagcaacaac ccactgagga gcatgtgctg  10920
aattatacat cacagcaccg cggccctgcc ctcatggcag ggctgcatgg cacccacagt  10980
ggcactcaga gggaccacag ggctgagaca gccgggtctg gtggtgggga cacagctgag  11040
cataggatga gccccccggg cagtgctggg ctttgctaat gagcagaagt atggatagaa  11100
agcaacccca gggctccgta cccagctgca gctcttgctc tgtcgtgtcc tttggtgaaa  11160
ctttaaacag tcgccttttt ttttctcttt cttttctggc ttgccattaa tttcaaaccg  11220
agagagacct aatttagtaa atgagatgct tcaggaaggc tttaattagc tgcagatgga  11280
ggcaggcagt gctatcgtgg ggcctggatc gcacaggggg ctgcatatcc tcactagcag  11340
aatacaccca ggctgggtcc ctcccacatt catgccccag accagaggga atatgctctg  11400
ttccccacac atctctccca atcttgcagc cgttgagccc caacatccca ccagcacacg  11460
gggctcagca cgcctggcga cgtggcatca gcagagcagg ccgcatggta cagctccatc  11520
agcacagctg gggccacaca aagagctggg ttactgtggg cagcaggctg aaacccgaaa  11580
acaagggctg gggggctcaga atagccctgg gagcaggcag ggcctggggg tgagggcaag  11640
caccaggccc agggccacac agcccttcca ggaaggcaca gcgctgtcag ggtgcagcac  11700
gctcagcccc accatgcagc tgtgcagccg gggcatcccc aagctaaatt tacttctcag  11760
tctccaatca gaaactgaag ctgaggggcc cacgccggcc aaaaaaagga aacgaaacag  11820
tctccagaaa gcactgacgt gtgaagcaga gcgagcgccg cgcaaaccag ccgccatgtc  11880
acacacctca ggttggggct ttgacagact gagctttgct gctgctcggg gtgggtgccc  11940
acggcctggg cacatgggat ggggtacaca agtacacaca cttgcacacc cacaccccaa  12000
cacttcaggt gatgctggtg cagatgggtg ccccccaggc tgaccccccc acgcgtgggc  12060
ctggccccac actgctccat ccgtgtctct gtccccatgt gccacccctg cccgctccca  12120
ccacgcgtca ccccaaatcc tgagttaatc ccacgactcc tgcctgcttc cagcatccat  12180
ggcagactgg agatgcccaa aatgcagagc aggtttccct gaatctgaga gatgaaatgg  12240
agttatgggt gttcccctgc ggcggagccc cagctgtagg aagctcagag ccatcacaca  12300
gcaattaaag aggaattaaa ttaaatcaat aaatgtttta ggcgggctca gctgccagca  12360
ccacctgacc gaaacagccc gcttgcaaag aggagagcat ttgcatggct gtggcaaaac  12420
agcaaccgcc tgttgtgcag ctgggatggt gttatctgga aatgtacgca gcccaggagg  12480
ggtaaacagc tccaaactga gaccccgagc ttgtccacag gttgtaaaca ggctgacata  12540
aacacctttg tgccgtggaa aaatatttat cacctcaaat atagcaggtt aataaaataa  12600
aactcccaac ggagctacac acctgctttg gaagggaagc agacacttgt tttctgcttg  12660
atgttggctg taggaaacca tgtttcccga tgcaggaggg ccacaaagca ctgacaacac  12720
aatgtgagct gagcttcgcc cctgtttaag cccccaccac agggcttgtg gcctcggagc  12780
aggcaggacg caggggtggc accgggctgg gtgacatggg ctggtcctgg ggtgtctcac  12840
tgagctcttt ggggaggggt tggagccctg gggcaatcac agcacacaca gaggaggtgg  12900
ggggatgcag ccagcagctg ccctgcacta agaaaacccc atccgtgggc tttcagatgg  12960
ccttcccatc tctctgcagc ctctgcatgg gctgagcgca aggtttaagt gtttctgcca  13020
tgtttttggg catgtttgga ggggcagcgt gggcccgggc atacgggtac cgccacgtgc  13080
```

-continued

```
tgccagcccc acagctgagc ctgcactctc ccagatgtgc tgaccgcagc cacgggggca  13140
acagtttctc ttgctaaaaa ttgtagccgg gaagaaaaca cgtggcaact tcggccaaac  13200
agcagctgga ggacaggaat agccgtggcc acggcacgct ctgcttcctc ggcacaaaca  13260
ttccagtacg tggcaccacg agcgccgctg cccggcacag cagcaagcag agccaggagc  13320
aggaaatgct gatttgggcc ccattttggc catggctgag agaagaggct tccagggagc  13380
tggtcagctt ggtccccaag ctgtggcttg gggaaatgat ggggaaggga ttgccactgc  13440
ccaccctgca gagcaggctc tggtcccatc tcactgcagg gcaccagggc gtttgcactg  13500
cagcaattca cagaaacacc tgaaatggct cctgtcttgt tcaacatctt catcagtgac  13560
ctggatgagg ggacagcatc caccatcagc gggttcactg atcatatgaa gtcgggaaga  13620
gtggctgacg caccacaagg ctgtgctgcc attcaacagg acgtggacag actggagagc  13680
tggacaggga ggaacccaat gaggttcaac aatggcaagt gtaggatcta cacctgggaa  13740
ggaataacag catgcatcag ttcaggttag gggctgagct gctgcagatg agctctgaga  13800
gaaggacctg agcgtcctgc tggacagcag gctggctgtg agccaccggt gtgccctggt  13860
ggccaagaag gccagtggta tcctggggag caccgcaatg agagtgggca gcagggcgag  13920
ggaggtgagg ctgcatttgg agcaccgtgc ccagttctgg gctcctcagt tcaaggcaga  13980
cagggaactg ctggagagag cccagcagag gggctgcaat gatgatgaag gtcctggagc  14040
atcgcctgta tgaggaaagg ctgagggacc tgggattgtt cagcttggag aagagaagac  14100
tacagggcag gagccaagtg gatagggccg ggctcttttc agcagtgccc attgacaagc  14160
caaggggcag caggcacaaa ctggaacata agaagttcca tctgaacatg aggaaaaact  14220
gcctcgcttt gagggtgtct gagcactgga agaagctgcc cagagaggtg gtggagtctc  14280
ctctggagat attcagagcc tggcaggaca ctttttgctg agtaacctac tgtagggaac  14340
ctgacgcagc agaggggtcg gactggagga tctccggagg tctctttcaa cccctacagt  14400
tccatgaaat acctcaaaca ctgccaagcg cagtgctaag gcaagggtaa catttgtaaa  14460
ctgaaacagg gtgggtttaa gttagatgta aagaagaaac tcttcactca gagggtggcg  14520
aggccctggc acaggctgcc catggaggct gcgggtgccc catccctggc agtgcccaag  14580
gcaagagccc agcagcgacc acagccccac aaggacgagc gtggcccctc gtatctcagc  14640
tcaccctgcc ccagctcaac ccccacctcc ggcacagcgc gggcacacag ccgggccctg  14700
tgcttatgga gcccttgggg caggtcagca ctcacaccct ccaaacacag ccgtggctcc  14760
caaccggagg cagctggatc tcggcagcca taaccaagca gggccatgcg ggggtgacac  14820
cggggtcccc cacccccctgt ggggcagcgt atgggctggg cccctgctcc agtctgcagc  14880
gtgtgcatgg gaaccatcat cagacaccac ctagaccacc cgcagcccta agctgcctca  14940
cagcagggat tgctccgtca caccgtgacc ccgtgccctt attccatcac ttatggggct  15000
gggagtgcct ggaccttggg cacattaacg aggatttccc gctctgccct cgctttgctc  15060
cgagccgtgg ggctgtgtag tgcagacaca gctgcagcct aaaattagca cctgggaaag  15120
gcccccatgc tgcaccgcac agggctgaga tgtgccacgt ccccatggcc ggagctgggg  15180
aaggcaacgt ggccctgtgc gtgtgcacgc tgagcacaag gacacgtgct gggccaggat  15240
ttgtctcccc ggggctcacg ctatgtgtca ccctgtgctg tgccatcccc tcccgcagcc  15300
cccagctccc ccacggccgc acgccgcctg catccctgca acggcaccgc acagagacac  15360
ggagccaggg gccgcacacg gggccaggag ctcaccttta ttgcagccct gacagcccca  15420
cggcccagcc cgcaccgggg ctgccacatc ctcacccgac cgacggcccc agctgctcct  15480
```

-continued

```
taccatttct tcccccatca cccataaacc agaagccgcc tcaccgctac gcggagcggg  15540
cagcagggaa cccgggccct aagggggaga cgagaggggg ccgagcaggg gcaggaggag  15600
cagcagggcg agggggcagc gggggcaccc acagctggac gtggcatctc gggaggagaa  15660
gaccttgcgg ctgcggagcg gttgtggcgg acggaagttg ttggtcatct tcaggggcgc  15720
agcgcccgag gccgggaagt gcacagtgct gacaaacgcc tgcagctgcg gggagagcac  15780
cgcgggcgcc gcagccgtga ggcgtagggc gaagcggggc acacgcgtgg ctgctgccgg  15840
gcagagcgca gcgcaggagc cccgtctttc cccctaccgg cagcacacgg ctctgcacac  15900
accgcgcttc gtgccgcctc gcagccgacg ctgcaggaag cccagccgag cgcttacaga  15960
gcggccggga aatgcatctg ctgaggtgcc cgggcaatgc agaacttcat ccatccccac  16020
atccattcac cagtcccctc ccaaaccccc atgcccatcc ggcgacccac ccaccctcct  16080
cttggtgccc ctctcaagct ctccatcccc acattcctac agatgtcccc tttactttgc  16140
ctgcaaggtg caagaaaacg cacagggacc gggggtgctc acagcacggc tttggccaga  16200
cgggcccttc catcccatgg cagcagggcc gaggaatccc attacctgct ccctgctgat  16260
gcccacaggc tcctcaaaca cggtccagat gacggcctcg ctgcagtcag gggtggtcag  16320
ggagccctgg tagcggtagt accgggacag ctgtgcaacg tgcggccgcc accgcggtgg  16380
agctccagct tttgttccct ttagtgaggg ttaattgcgc gcttggcgta atcatggtca  16440
tagctgtttc ctgtgtgaaa ttgttatccg ctcacaattc cacacaacat acgagccgga  16500
agcataaagt gtaaagcctg gggtgcctaa tgagtgagct aactcacatt aattgcgttg  16560
cgctcactgc ccgctttcca gtcgggaaac ctgtcgtgcc agctgcatta atgaatcggc  16620
caacgcgcgg ggagaggcgg tttgcgtatt gggcgctctt ccgcttcctc gctcactgac  16680
tcgctgcgct cggtcgttcg gctgcggcga gcggtatcag ctcactcaaa ggcggtaata  16740
cggttatcca cagaatcagg ggataacgca ggaaagaaca tgtgagcaaa aggccagcaa  16800
aaggccagga accgtaaaaa ggccgcgttg ctggcgtttt tccataggct ccgcccccct  16860
gacgagcatc acaaaaatcg acgctcaagt cagaggtggc gaaacccgac aggactataa  16920
agataccagg cgtttccccc tggaagctcc ctcgtgcgct ctcctgttcc gaccctgccg  16980
cttaccggat acctgtccgc ctttctccct tcgggaagcg tggcgctttc tcatagctca  17040
cgctgtaggt atctcagttc ggtgtaggtc gttcgctcca agctgggctg tgtgcacgaa  17100
ccccccgttc agcccgaccg ctgcgcctta tccggtaact atcgtcttga gtccaacccg  17160
gtaagacacg acttatcgcc actggcagca gccactggta acaggattag cagagcgagg  17220
tatgtaggcg gtgctacaga gttcttgaag tggtggccta actacggcta cactagaagg  17280
acagtatttg gtatctgcgc tctgctgaag ccagttacct tcggaaaaag agttggtagc  17340
tcttgatccg gcaaacaaac caccgctggt agcggtggtt tttttgtttg caagcagcag  17400
attacgcgca gaaaaaaagg atctcaagaa gatcctttga tcttttctac ggggtctgac  17460
gctcagtgga acgaaaactc acgttaaggg attttggtca tgagattatc aaaaaggatc  17520
ttcacctaga tccttttaaa ttaaaaatga agttttaaat caatctaaag tatatatgag  17580
taaacttggt ctgacagtta ccaatgctta atcagtgagg cacctatctc agcgatctgt  17640
ctatttcgtt catccatagt tgcctgactc cccgtcgtgt agataactac gatacgggag  17700
ggcttaccat ctggccccag tgctgcaatg ataccgcgag acccacgctc accggctcca  17760
gatttatcag caataaacca gccagccgga agggccgagc gcagaagtgg tcctgcaact  17820
```

-continued

```
ttatccgcct ccatccagtc tattaattgt tgccgggaag ctagagtaag tagttcgcca  17880

gttaatagtt tgcgcaacgt tgttgccatt gctacaggca tcgtggtgtc acgctcgtcg  17940

tttggtatgg cttcattcag ctccggttcc caacgatcaa ggcgagttac atgatccccc  18000

atgttgtgca aaaaagcggt tagctccttc ggtcctccga tcgttgtcag aagtaagttg  18060

gccgcagtgt tatcactcat ggttatggca gcactgcata attctcttac tgtcatgcca  18120

tccgtaagat gcttttctgt gactggtgag tactcaacca agtcattctg agaatagtgt  18180

atgcggcgac cgagttgctc ttgcccggcg tcaatacggg ataataccgc gccacatagc  18240

agaactttaa aagtgctcat cattggaaaa cgttcttcgg ggcgaaaact ctcaaggatc  18300

ttaccgctgt tgagatccag ttcgatgtaa cccactcgtg cacccaactg atcttcagca  18360

tcttttactt tcaccagcgt ttctgggtga gcaaaaacag gaaggcaaaa tgccgcaaaa  18420

aagggaataa gggcgacacg gaaatgttga atactcatac tcttcctttt tcaatattat  18480

tgaagcattt atcagggtta ttgtctcatg agcggataca tatttgaatg tatttagaaa  18540

aataaacaaa taggggttcc gcgcacattt ccccgaaaag tgccac                18586
```

<210> SEQ ID NO 6
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 6

```
cagtgtccaa attccttaaa tttcc                                          25
```

<210> SEQ ID NO 7
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 7

```
atacgatgtt ccagattacg ctt                                            23
```

<210> SEQ ID NO 8
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 8

```
tgaacccata aagtgaaatc ctc                                            23
```

<210> SEQ ID NO 9
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 9

```
ttcggtcccg tggccccat                                                 19
```

<210> SEQ ID NO 10
<211> LENGTH: 22
<212> TYPE: DNA
<213> ORGANISM: artificial sequence
<220> FEATURE:
<223> OTHER INFORMATION: Synthetic oligonucleotide

<400> SEQUENCE: 10
ggaacacggc ggcatcagag ca 22

<210> SEQ ID NO 11
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 11
ccggaaagca aaatttgggg gcaa 24

<210> SEQ ID NO 12
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 12
gggggttcgg tgcagttttt c 21

<210> SEQ ID NO 13
<211> LENGTH: 23
<212> TYPE: DNA
<213> ORGANISM: artificial sequence
<220> FEATURE:
<223> OTHER INFORMATION: Synthetic oligonucleotide

<400> SEQUENCE: 13
atattggccc catttcccct cag 23

<210> SEQ ID NO 14
<211> LENGTH: 14762
<212> TYPE: DNA
<213> ORGANISM: artificial sequence
<220> FEATURE:
<223> OTHER INFORMATION: Synthetic vector construct

<400> SEQUENCE: 14
ctaaattgta agcgttaata ttttgttaaa attcgcgtta aatttttgtt aaatcagctc 60 atttttttaac caataggccg aaatcggcaa aatcccttat aaatcaaaag aatagaccga 120
gatagggttg agtgttgttc cagtttggaa caagagtcca ctattaaaga acgtggactc 180
caacgtcaaa gggcgaaaaa ccgtctatca gggcgatggc ccactacgtg aaccatcacc 240
ctaatcaagt tttttggggt cgaggtgccg taaagcacta aatcggaacc ctaaagggag 300
cccccgattt agagcttgac ggggaaagcc ggcgaacgtg gcgagaaagg aagggaagaa 360
agcgaaagga gcgggcgcta gggcgctggc aagtgtagcg gtcacgctgc gcgtaaccac 420
cacacccgcc gcgcttaatg cgccgctaca gggcgcgtcc cattcgccat tcaggctgcg 480
caactgttgg gaagggcgat cggtgcgggc ctcttcgcta ttacgccagc tggcgaaagg 540
gggatgtgct gcaaggcgat taagttgggt aacgccaggg ttttcccagt cacgacgttg 600
taaaacgacg gccagtgagc gcgcgtaata cgactcacta tagggcgaat tgggtaccgg 660
cgcgcctggg aaatttggcc ctcttggccc aattttgccc aaaaatggca aaatttgggg 720
tcatttcttc ccccgtaggt gagagcttca acctccagca gctccacgac tccaaaaaag 780

-continued

```
agacattttg cccattttct gccatttttt gacccaaatt ttggggtctt ttccccttcc    840
acggccactt tgaaacccta caaattactg cctctttttt tctccgtttt ttgccccaaa    900
tctgcctttt tttccccct ttttggggcc ctccgggagg aaacgtctcc accggtggcc    960
gctcaagtgg tgaacccaca aactttgggg taaaaacaca ggattttggt caacgttgta   1020
tcactgtggg ttgtagtgct tacggttgtg gtgcttatca cggtgctcca tcccataaca   1080
aaaaccatcc tcattttggg gcaactttgg ccctttttgg tcaatttttg ccccccacgt   1140
acgacgattt ccccctcttc tttggccacc attgacccaa aatttggggt tattttcccc   1200
ctttttacca atattaccaa aaaaaaatca atttttccca tcttccccag accacaaaat   1260
tgggattttt ttttggcctt tttcggctat tttttgcccc aaaatccaac gattcccctc   1320
tcctcctcac ctccaaaaat ggggccattt tgtccctttt ccccattttc cacccccttt   1380
cccccccctc tccacattta cagtttttgg acgctcccaa tcttgccccg ttttgcccca   1440
aaatccccct ctttccaggc attcgatccc aaaattgaga tatttgatca tttttaacca   1500
ttttccccca aaataccgcc tcctcactga cggccgcggt gccaaaaacg ggaattttc   1560
tcccaaatac gttcaatgtt ttccctttttt ttgcccgttt ttgaccggtt ttgcccattt   1620
ttgtgcgttt ttaaccattt ttttttacat tttttaacca aatttgtgtg tttttacctt   1680
aagattcagc tcccatgggt gaaaaatgag aggtttctcc ccattcaaat tctacgactt   1740
ttgggatatc cctacgtgga gaatttgggg taaaaatgcc acaaatcggt taaaaatggc   1800
attttttggc taaaaaatgg catttttttgt tctgaaaata gcatttttttg gctaaaattg   1860
ggggttttag ccctaaaata gggaggaaaa caatgaggat ttgaaacact ccgtccccaa   1920
aattgaaatc tttgattctg gcatcattgg gtgatccgaa gtgaggaatt tggggtaaaa   1980
atggctcaaa ttggttaaaa ataaccgttt ttggtctgaa aatggcattt ttttggctaa   2040
aattggggtt tttagcccta aaatagggag gaaaacagtg aggatttgaa aactctgaac   2100
ccataaagtg aaatcctcaa ttttggcat cattgggtga tcttaaggga ggaatttggg   2160
gcaaaaatgg ccaaattggt taagaatagc agtttttggt ctaaaaatgg catttttttgg   2220
ctaaaattgg ggtttttagc cctaaaatgg ggaggaatcc aatgaggatt tgaaacactc   2280
cgagcccaga attgaaatct tcgattttgg tcatctttgg gtgattctaa cggaggaatt   2340
tggggtaaaa acagcccaaa ttggttaaaa atggcagttt ttggtctaaa aatggcagtt   2400
tttgttctga aaatggcatt ttttggctaa aattggggtt ttttgcccta aaatagtgag   2460
gaaaacaaca aggatttgaa aaacctgaag gcaaacaatg aaatcttcga ttttgggcca   2520
atattgcagg aatttggagc gaaggatggc caaaaaaacgg ttgtttttttt cttttttaac   2580
caaaatgggc ggttttcgcc ccgagctagc ataacttcgt atagcataca ttatacgaag   2640
ttataagcgt aatctggaac atcgtatgta ccggatccga agcaggcttt cctggaaggt   2700
cctggaaggg ggcgtccgcg ggagctcacg gggacagccc ccccccaaag cccccaggga   2760
tgtaattacg tccctccccc gctagggggc agcagcgagc cgcccggggc tccgctccgg   2820
tccggcgctc ccccgcatc cccgagccgg cagcgtgcgg ggacagcccg ggcacgggga   2880
aggtggcacg ggatcgcttt cctctgaacg cttctcgctg ctctttgagc ctgcagacac   2940
ctgggggat acggggaaaa agctttaggc tgagaagcag gctttcctgg aaggtcctgg   3000
aagggggcgt ccgcgggagc tcacggggac agcccccccc caaagccccc agggatgtaa   3060
ttacgtccct cccccgctag gggcagcag cgagccgccc ggggctccgc tccggtccgg   3120
cgctcccccc gcatccccga gccggcagcg tgcggggaca gcccgggcac ggggaaggtg   3180
```

-continued

```
gcacgggatc gctttcctct gaacgcttct cgctgctctt tgagcctgca gacacctggg   3240
gggatacggg gaaaaagctt taggctgaac tagctagtct cgaggtcgag gtgagcccca   3300
cgttctgctt cactctcccc atctcccccc cctccccacc cccaattttg tatttattta   3360
tttttaatt attttgtgca gcgatggggg cggggggggg gggggcgcgc gccaggcggg   3420
gcggggcggg gcgaggggcg gggcggggcg aggcggagag gtgcggcggc agccaatcag   3480
agcggcgcgc tccgaaagtt tccttttatg gcgaggcggc ggcggcggcg gccctataaa   3540
aagcgaagcg cgcggcgggc gggagtcgct gcgttgcctt cgccccgtgc cccgctccgc   3600
gccgcctcgc gccgcccgcc ccggctctga ctgaccgcgt tactcccaca ggtgagcggg   3660
cgggacggcc cttctcctcc gggctgtaat tagcgcttgg tttaatgacg gctcgtttct   3720
tttctgtggc tgcgtgaaag ccttaaaggg ctccgggagg gccctttgtg cggggggggag   3780
cggctcgggg ggtgcgtgcg tgtgtgtgtg cgtggggagc gccgcgtgcg gcccgcgctg   3840
cccggcggct gtgagcgctg cgggcgcggc gcggggcttt gtgcgctccg cgtgtgcgcg   3900
aggggagcgc ggccgggggc ggtgccccgc ggtgcggggg ggctgcgagg ggaacaaagg   3960
ctgcgtgcgg ggtgtgtgcg tgggggggtg agcagggggt gtgggcgcgg cggtcgggct   4020
gtaacccccc cctgcacccc cctccccgag ttgctgagca cggcccggct tcgggtgcgg   4080
ggctccgtgc ggggcgtggc gcggggctcg ccgtgccggg cggggggtgg cggcaggtgg   4140
gggtgccggg cggggcgggg ccgcctcggg ccggggaggg ctcgggggag ggcgcggcg   4200
gccccggagc gccggcggct gtcgaggcgc ggcgagccgc agccattgcc ttttatggta   4260
atcgtgcgag agggcgcagg gacttccttt gtcccaaatc tggcggagcc gaaatctggg   4320
aggcgccgcc gcaccccctc tagcgggcgc gggcgaagcg gtgcggcgcc ggcaggaagg   4380
aaatgggcgg ggagggcctt cgtgcgtcgc cgcgccgccg tccccttctc catctccagc   4440
ctcggggctg ccgcaggggg acggctgcct tcgggggga cggggcaggg cggggttcgg   4500
cttctggcgt gtgaccggcg gctctagagc ctctgctaac catgttcatg ccttcttctt   4560
tttcctacag ctcctgggca acgtgctggt tgttgtgctg tctcatcatt ttggcaaaga   4620
attatcgcat gcctgcgtcg acggtaccgc gggcccggga tccaccggtc gccaccatgg   4680
tgagcaaggg cgaggagctg ttcaccgggg tggtgcccat cctggtcgag ctggacggcg   4740
acgtaaacgg ccacaagttc agcgtgtccg gcgagggcga gggcgatgcc acctacggca   4800
agctgaccct gaagttcatc tgcaccaccg gcaagctgcc cgtgccctgg cccaccctcg   4860
tgaccaccct gacctacggc gtgcagtgct tcagccgcta ccccgaccac atgaagcagc   4920
acgacttctt caagtccgcc atgcccgaag gctacgtcca ggagcgcacc atcttcttca   4980
aggacgacgg caactacaag acccgcgccg aggtgaagtt cgagggcgac accctggtga   5040
accgcatcga gctgaagggc atcgacttca aggaggacgg caacatcctg gggcacaagc   5100
tggagtacaa ctacaacagc cacaacgtct atatcatggc cgacaagcag aagaacggca   5160
tcaaggtgaa cttcaagatc cgccacaaca tcgaggacgg cagcgtgcag ctcgccgacc   5220
actaccagca gaacaccccc atcggcgacg gccccgtgct gctgcccgac aaccactacc   5280
tgagcaccca gtccgccctg agcaaagacc ccaacgagaa gcgcgatcac atggtcctgc   5340
tggagttcgt gaccgccgcc gggatcactc tcggcatgga cgagctgtac aagtaaagcg   5400
gccggccgcg actctagatc ataatcagcc ataccacatt tgtagaggtt ttacttgctt   5460
taaaaaacct cccacacctc cccctgaacc tgaaacataa aatgaatgca attgttgttg   5520
```

-continued

```
ttaacttgtt tattgcagct tataatggtt acaaataaag caatagcatc acaaatttca   5580
caaataaagc atttttttca ctgcattcta gttgtggttt gtccaaactc atcaatgtat   5640
cttaaggaac ccttcctcg acattgatta ttgactagct agttattaat agtaatcaat   5700
tacggggtca ttagttcata gcccatatat ggagttccgc gttacataac ttacggtaaa   5760
tggcccgcct ggctgaccgc ccaacgaccc ccgcccattg acgtcaataa tgacgtatgt   5820
tcccatagta acgccaatag ggactttcca ttgacgtcaa tgggtggact atttacggta   5880
aactgcccac ttggcagtac atcaagtgta tcatatgcca agtacgcccc ctattgacgt   5940
caatgacggt aaatggcccg cctggcatta tgcccagtac atgaccttat gggactttcc   6000
tacttggcag tacatctacg tattagtcat cgctattacc atgggtcgag gtgagcccca   6060
cgttctgctt cactctcccc atctcccccc cctccccacc cccaattttg tatttattta   6120
tttttaatt attttgtgca gcgatggggg cgggggggg gggggcgcgc gccaggcggg   6180
gcggggcggg gcgaggggcg gggcggggcg aggcggagag gtgcggcggc agccaatcag   6240
agcggcgcgc tccgaaagtt tccttttatg gcgaggcggc ggcggcggcg gccctataaa   6300
aagcgaagcg cgcggcgggc gggagtcgct gcgttgcctt cgccccgtgc cccgctccgc   6360
gccgcctcgc gccgcccgcc ccggctctga ctgaccgcgt tactcccaca ggtgagcggg   6420
cgggacggcc cttctcctcc gggctgtaat tagcgcttgg tttaatgacg gctcgtttct   6480
tttctgtggc tgcgtgaaag ccttaaaggg ctccgggagg gccctttgtg cggggggag   6540
cggctcgggg ggtgcgtgcg tgtgtgtgtg cgtggggagc gccgcgtgcg gcccgcgctg   6600
cccggcggct gtgagcgctg cgggcgcggc gcggggcttt gtgcgctccg cgtgtgcgcg   6660
aggggagcgc ggccgggggc ggtgccccgc ggtgcggggg ggctgcgagg ggaacaaagg   6720
ctgcgtgcgg ggtgtgtgcg tgggggggtg agcagggggt gtgggcgcgg cggtcgggct   6780
gtaacccccc cctgcacccc cctccccgag ttgctgagca cggcccggct tcgggtgcgg   6840
ggctccgtgc ggggcgtggc gcggggctcg ccgtgccggg cgggggtgg cggcaggtgg   6900
gggtgccggg cggggcgggg ccgcctcggg ccggggaggg ctcgggggag ggcgcggcg   6960
gccccggagc gccggcggct gtcgaggcgc ggcgagccgc agccattgcc ttttatggta   7020
atcgtgcgag agggcgcagg gacttccttt gtcccaaatc tggcggagcc gaaatctggg   7080
aggcgccgcc gcacccccct tagcgggcgc gggcgaagcg gtgcggcgcc ggcaggaagg   7140
aaatgggcgg ggagggcctt cgtgcgtcgc cgcgccgccg tccccttctc catctccagc   7200
ctcggggctg ccgcaggggg acggctgcct tcggggggga cggggcaggg cggggttcgg   7260
cttctggcgt gtgaccggcg gctctagagc ctctgctaac catgttcatg ccttcttctt   7320
tttcctacag ctcctgggca acgtgctggt tattgtgctg tctcatcatt ttggcaaaga   7380
attcctagcg ccaccatgac cgagtacaag cctaccgtgc gcctggccac tcgcgatgat   7440
gtgccccgcg ccgtccgcac tctggccgcc gctttcgccg actaccccgc tacccggcac   7500
accgtggacc ccgaccggca catcgagcgt gtgacagagt tgcaggagct gttcctgacc   7560
cgcgtcgggc tggacatcgg caaggtgtgg gtagccgacg acggcgcggc cgtggccgtg   7620
tggactaccc ccgagagcgt tgaggccggc gccgtgttcg ccgagatcgg cccccgaatg   7680
gccgagctga gcggcagccg cctggccgcc cagcagcaaa tggagggcct gcttgccccc   7740
catcgtccca aggagcctgc ctggtttctg gccactgtag gagtgagccc cgaccaccag   7800
ggcaagggct tgggcagcgc cgtcgtgttg cccggcgtag aggccgccga acgcgccggt   7860
gtgcccgcct ttctcgaaac aagcgcacca agaaaccttc cattctacga gcgcctgggc   7920
```

-continued

```
ttcaccgtga ccgccgatgt cgaggtgccc gagggaccta ggacctggtg tatgacacga   7980
aaacctggcg cctaatgatc tagaaccggt catggccgca ataaaatatc tttattttca   8040
ttacatctgt gtgttggttt tttgtgtgtt cgaacctgca gcccggggga tccgaagcag   8100
gctttcctgg aaggtcctgg aagggggcgt ccgcgggagc tcacggggac agcccccccc   8160
caaagccccc agggatgtaa ttacgtccct cccccgctag gggggcagcag cgagccgccc   8220
ggggctccgc tccggtccgg cgctcccccc gcatccccga gccggcagcg tgcggggaca   8280
gcccgggcac ggggaaggtg gcacgggatc gctttcctct gaacgcttct cgctgctctt   8340
tgagcctgca gacacctggg gggatacggg gaaaaagctt taggctgaga agcaggcttt   8400
cctggaaggt cctggaaggg ggcgtccgcg ggagctcacg ggacagcccc ccccccaaag   8460
cccccaggga tgtaattacg tccctccccc gctagggggc agcagcgagc cgcccggggc   8520
tccgctccgg tccggcgctc ccccgcatc cccgagccgg cagcgtgcgg ggacagcccg   8580
ggcacgggga aggtggcacg ggatcgcttt cctctgaacg cttctcgctg ctctttgagc   8640
ctgcagacac ctggggggat acggggaaaa agctttaggc tgaactagaa tgcatataac   8700
ttcgtatagc atacattata cgaagttatg gatcccccaa atcaatctaa agtatatatg   8760
agtaacctga ggctatggca gggcctgccg ccccgacgtt ggctgcgagc cctgggcctt   8820
cacccgaact tggggggtgg ggtggggaaa aggaagaaac gcgggcgtat tggccccaat   8880
ggggtctcgg tggggtatcg acagagtgcc agccctggga ccgaaccccg cgtttatgaa   8940
caaacgaccc aacaccgtgc gttttattct gtctttttat tgccgtcata gcgcgggttc   9000
cttccggtat tgtctccttc cgtgtttcag ttagcctccc cctagggtgg gcgaagaact   9060
ccagcatgag atccccgcgc tggaggatca tccagccggc gtcccggaaa acgattccga   9120
agcccaacct ttcatagaag gcggcggtgg aatcgaaatc tcgtgatggc aggttgggcg   9180
tcgcttggtc ggtcatttcg aaccccagag tcccgctcag aagaactcgt caagaaggcg   9240
atagaaggcg atgcgctgcg aatcgggagc ggcgataccg taaagcacga ggaagcggtc   9300
agcccattcg ccgccaagct cttcagcaat atcacgggta gccaacgcta tgtcctgata   9360
gcggtccgcc acacccagcc ggccacagtc gatgaatcca gaaaagcggc cattttccac   9420
catgatattc ggcaagcagg catcgccatg ggtcacgacg agatcctcgc cgtcgggcat   9480
gctcgccttg agcctggcga acagttcggc tggcgcgagc ccctgatgct cttcgtccag   9540
atcatcctga tcgacaagac cggcttccat ccgagtacgt gctcgctcga tgcgatgttt   9600
cgcttggtgg tcgaatgggc aggtagccgg atcaagcgta tgcagccgcc gcattgcatc   9660
agccatgatg gatactttct cggcaggagc aaggtgagat gacaggagat cctgccccgg   9720
cacttcgccc aatagcagcc agtcccttcc cgcttcagtg acaacgtcga gcacagctgc   9780
gcaaggaacg cccgtcgtgg ccagccacga tagccgcgct gcctcgtctt gcagttcatt   9840
cagggcaccg gacaggtcgg tcttgacaaa aagaaccggg cgcccctgcg ctgacagccg   9900
gaacacggcg gcatcagagc agccgattgt ctgttgtgcc cagtcatagc cgaatagcct   9960
ctccacccaa gcggccggag aacctgcgtg caatccatct tgttcaatca tgcgaaacga  10020
tcctcatcct gtctcttgat cgattacgcc cccaactgag agaactcaaa ggttacccca  10080
gttggggcac actagtggcg gtctgagggg aaaatgtcgt tttggggcca ttttgggcca  10140
tttgagggga aatttgggtc aaaaaatgac gattttgggt cattttaggg ataaaaaatg  10200
aatttaggga gatttgaggg caaatttggg tcaaaaaatg gtgatttggg gtcaaaaatg  10260
```

-continued

```
gacaattttg ggtcatttta gggttaaaaa tggatttagg gaaatttgat ggcaaatttg  10320
ggtcaaaaaa tggtgatttt gggtcaaaaa atgattattt tgggtcattt tagggagaaa  10380
aatgaattta gggagatttg agggcaaatt tgggtcgaaa aatggtgatt ttgggtgaaa  10440
aatggacaat tttgggtcat tttagggtta aaaatgaatt tagggagatt ggacggcaaa  10500
tttgggtcaa aaaatggtga tttggggtca aaaaataatt attttgggtc attttaggga  10560
taaaaaatga atttagggag atttgagggc aaatttgggt cgaaaaaatgg tgattttggg  10620
tgaaaaatgg acaattttgg gtcattttag ggataaaaaa tgaatttagg gcgatttgag  10680
ccaaatttgg gtcaaaaatg gtgattttgg gtgaaaaatt gacagttttg ggtcatttta  10740
gggttaaaaa tgaatttagg gagattggac ggcaaatttg ggtcaaaaaa tggtgatttg  10800
gggtcaaaaa atgattattt tgggtcattt tagggataaa aaatgaattt agggagatgt  10860
gagggcaaat ttgggtcgaa aaatggtgat tttgggtgaa aaattgacag ttttgggtca  10920
ttttagggat ataaatggac ttagagagat ttgagggcaa atttgggtga aaaaatggac  10980
aatttgggtc atttttggga tataaatgaa tttaagattt gacggcaaat ttgggtcaaa  11040
aaatggtgat ttgggtcaaa aatggtgatt ttggttgaaa aacggccatt ttgggtcatt  11100
ttagggataa aaatgaattt agggagattt gagggcaaat ttgggtgaaa aaagggcgat  11160
ttgggggtca ttttagggag aaaaaatgaat ttagggcgat ttgagggcaa atttgggtga  11220
aaaaagggag atttttggtc attttaggga taaaaatgaa tttagggaga actgagggca  11280
aatttgggtc aaaaaatgac aatttgggtc gttctaggga gaaaaatgaa ttttgggcga  11340
tttgagggta aatttgggtc gaaaaatggt gatttgggtc aaaaaatgat tattttgggt  11400
catttaaggg agaaaaggga tttagggaga tttgagggca aatttgggtc gaaaaattgt  11460
gatttggggt caaaaaatga caattttggg tcattttagg gatataaatg gacttagagc  11520
gatttgaggg caaatttggg tgaaaaaatg acaatttggg tcattttagg gatataaatg  11580
aatttagggc gatttgaggg caaatttggt tcgaaaatgg tgattttggg tcaatttagg  11640
gaggaaaatg aatttaaggc aatttgaagg caaatttggg tgaaaaaatg acaatttggg  11700
gtcattttaa agataaaatg aatttagggc tatttgaggg caaatttggg tcaaaaaatg  11760
gtgatttggg gtcaaaaaat atggtgattt tgagtcgttt tagggggggaa aatgaattta  11820
gggagatttg agggcaaatt tgggtcaaaa aatggtgatt tttggtcgtt ttagtgataa  11880
aaaatgaatt tagggcagtt tgagggcaaa tctgggtcaa aaaagggtga ttttgagtca  11940
aaaatagtga ttttgggtca ttttagggat ataaatgaat tcagggagat ttgagggcaa  12000
atttgagtca aaaatagtga tatgggtcaa aagtggtgat tttggttgaa aaacagtcat  12060
tttgggtcat tttagggatt aaaatgaact tagggagatt tgagggcaaa tttgggtcaa  12120
aaaatgacaa ttttgggtca ctttacgaat taaaatgaat tcagggagat ttgagggcaa  12180
atttgggtca aaaaaatggt gattttgggt cattttaggg ttaaaaatga attcaggatg  12240
atttgaaggc aactttgggt caaaaaaatg attatttggg tcattttaaa gaggaaaatg  12300
aatttaggga gatttgaggg caaattcggg tgaaaattgg acaattttgg gtcattttag  12360
ggataaaaat gaatttaggg agatttgagg gcaaatttgg gtcaaaaaat ggtgattttg  12420
ggtcgtttta ggaataaaaa tgaatttagg gagatttgag ggcaaatttg ggtcaaaaaa  12480
tggtgatttg gggtcatttt cagaaggaaa atgattattt tccccactaa aaatgtagcg  12540
gccgccaccg cggtggagct ccagcttttg ttccctttag tgagggttaa ttgcgcgctt  12600
ggcgtaatca tggtcatagc tgtttcctgt gtgaaattgt tatccgctca caattccaca  12660
```

-continued

```
caacatacga gccggaagca taaagtgtaa agcctggggt gcctaatgag tgagctaact  12720
cacattaatt gcgttgcgct cactgcccgc tttccagtcg ggaaacctgt cgtgccagct  12780
gcattaatga atcggccaac gcgcggggag aggcggtttg cgtattgggc gctcttccgc  12840
ttcctcgctc actgactcgc tgcgctcggt cgttcggctg cggcgagcgg tatcagctca  12900
ctcaaaggcg gtaatacggt tatccacaga atcaggggat aacgcaggaa agaacatgtg  12960
agcaaaaggc cagcaaaagg ccaggaaccg taaaaaggcc gcgttgctgg cgtttttcca  13020
taggctccgc ccccctgacg agcatcacaa aaatcgacgc tcaagtcaga ggtggcgaaa  13080
cccgacagga ctataaagat accaggcgtt tccccctgga agctccctcg tgcgctctcc  13140
tgttccgacc ctgccgctta ccggatacct gtccgccttt ctcccttcgg gaagcgtggc  13200
gctttctcat agctcacgct gtaggtatct cagttcggtg taggtcgttc gctccaagct  13260
gggctgtgtg cacgaacccc ccgttcagcc cgaccgctgc gccttatccg gtaactatcg  13320
tcttgagtcc aacccggtaa gacacgactt atcgccactg gcagcagcca ctggtaacag  13380
gattagcaga gcgaggtatg taggcggtgc tacagagttc ttgaagtggt ggcctaacta  13440
cggctacact agaaggacag tatttggtat ctgcgctctg ctgaagccag ttaccttcgg  13500
aaaaagagtt ggtagctctt gatccggcaa acaaaccacc gctggtagcg gtggtttttt  13560
tgtttgcaag cagcagatta cgcgcagaaa aaaaggatct caagaagatc ctttgatctt  13620
ttctacgggg tctgacgctc agtggaacga aaactcacgt taagggattt tggtcatgag  13680
attatcaaaa aggatcttca cctagatcct tttaaattaa aaatgaagtt ttaaatcaat  13740
ctaaagtata tatgagtaaa cttggtctga cagttaccaa tgcttaatca gtgaggcacc  13800
tatctcagcg atctgtctat ttcgttcatc catagttgcc tgactccccg tcgtgtagat  13860
aactacgata cgggagggct taccatctgg ccccagtgct gcaatgatac cgcgagaccc  13920
acgctcaccg gctccagatt tatcagcaat aaaccagcca gccggaaggg ccgagcgcag  13980
aagtggtcct gcaactttat ccgcctccat ccagtctatt aattgttgcc gggaagctag  14040
agtaagtagt tcgccagtta atagtttgcg caacgttgtt gccattgcta caggcatcgt  14100
ggtgtcacgc tcgtcgtttg gtatggcttc attcagctcc ggttcccaac gatcaaggcg  14160
agttacatga tcccccatgt tgtgcaaaaa agcggttagc tccttcggtc ctccgatcgt  14220
tgtcagaagt aagttggccg cagtgttatc actcatggtt atggcagcac tgcataattc  14280
tcttactgtc atgccatccg taagatgctt ttctgtgact ggtgagtact caaccaagtc  14340
attctgagaa tagtgtatgc ggcgaccgag ttgctcttgc ccggcgtcaa tacgggataa  14400
taccgcgcca catagcagaa ctttaaaagt gctcatcatt ggaaaacgtt cttcggggcg  14460
aaaactctca aggatcttac cgctgttgag atccagttcg atgtaaccca ctcgtgcacc  14520
caactgatct tcagcatctt ttactttcac cagcgtttct gggtgagcaa aaacaggaag  14580
gcaaaatgcc gcaaaaaagg gaataagggc gacacggaaa tgttgaatac tcatactctt  14640
cctttttcaa tattattgaa gcatttatca gggttattgt ctcatgagcg gatacatatt  14700
tgaatgtatt tagaaaaata aacaaatagg ggttccgcgc acatttcccc gaaaagtgcc  14760
ac                                                                 14762
```

<210> SEQ ID NO 15
<211> LENGTH: 9736
<212> TYPE: DNA
<213> ORGANISM: Gallus gallus -continued

<400> SEQUENCE: 15

```
cagtgtccaa attccttaaa tttcctcatt tttgcccatt ttgccccgaa ataccacacc     60
cttaatgccc tcccggcccc ccccagaatg gagcatttta cactttttgc ccatttttgc    120
tcaaattttg cgtgttttcc tgcggttttg gtcagcgact ctttgaacgt tggggatatt    180
ttgccatttt ttgatgtttt tgcccaaaat ggaaatattt cgctctcact ctcaacgtcc    240
ccccaaaaaa tgggctattt tccccatttt cccccatttt ttttatcgaa atcaccgtta    300
tttctacgaa attttcaccg catttcacaa cgatgggaaa tttggccctc ttggcccaat    360
tttgcccaaa aatggcaaaa tttggggtca tttcttcccc cgtaggtgag agcttcaacc    420
tccagcagct ccacgactcc aaaaaagaga cattttgccc attttctgcc atttttttgac    480
ccaaattttg gggtcttttc cccttccacg gccactttga aaccctacaa attactgcct    540
cttttttctt ccgtttttttg ccccaaatct gccttttttt cccccctttt tggggccctc    600
cgggaggaaa cgtctccacc ggtggccgct caagtggtga acccacaaac tttggggtaa    660
aaacacagga ttttggtcaa cgttgtatca ctgtgggttg tagtgcttac ggttgtggtg    720
cttatcacgg tgctccatcc cataacaaaa accatcctca ttttggggca actttggccc    780
tttttggtca atttttgccc cccacgtacg acgatttccc cctcttcttt ggccaccatt    840
gacccaaaat ttggggttat tttccccctt tttaccaata ttaccaaaaa aaaatcaatt    900
tttcccatct tccccagacc acaaaattgg gattttttttt tggccttttt cggctatttt    960
ttgccccaaa atccaacgat tcccctctcc tcctcacctc caaaaatggg gccattttgt   1020
ccctttttccc cattttccac cccctttccc ccccctctcc acatttacag tttttggacg   1080
ctcccaatct tgccccgttt tgccccaaaa tccccctctt tccaggcatt cgatcccaaa   1140
attgagatat ttgatcattt ttaaccattt tcccccaaaa taccgcctcc tcactgacgg   1200
ccgcggtgcc aaaaacgggg aattttctcc caaatacgtt caatgttttc ccttttttttg   1260
cccgtttttg accggttttg cccatttttg tgcgttttta accatttttt tttacatttt   1320
ttaaccaaat ttgtgtgttt ttaccttaag attcagctcc catgggtgaa aaatgagagg   1380
tttctcccca ttcaaattct acgacttttg ggatatccct acgtggagaa tttggggtaa   1440
aaatgccaca aatcggttaa aaatggcatt ttttggctaa aaaatggcat tttttgttct   1500
gaaaatagca ttttttggct aaaattgggg gttttagccc taaaataggg aggaaaacaa   1560
tgaggatttg aaacactccg tccccaaaat tgaaatcttt gattctggca tcattgggtg   1620
atccgaagtg aggaatttgg ggtaaaaatg gctcaaattg gttaaaaata accgtttttg   1680
gtctgaaaat ggcatttttt tggctaaaat tggggttttt agccctaaaa tagggaggaa   1740
aacagtgagg atttgaaaac tctgaaccca taaagtgaaa tcctcaattt tgggcatcat   1800
tgggtgatct taagggagga atttggggca aaaatggcca aattggttaa gaatagcagt   1860
ttttggtcta aaaatggcat tttttggcta aaattggggt ttttagccct aaaatgggga   1920
ggaatccaat gaggatttga aacactccga gcccagaatt gaaatcttcg attttggtca   1980
tctttgggtg attctaacgg aggaatttgg ggtaaaaaca gcccaaattg gttaaaaatg   2040
gcagtttttg gtctaaaaat ggcagttttt gttctgaaaa tggcattttt tggctaaaat   2100
tggggttttt tgccctaaaa tagtgaggaa aacaacaagg atttgaaaaa cctgaaggca   2160
aacaatgaaa tcttcgattt tgggccaata ttgcaggaat ttggagcgaa ggatggccaa   2220
aaaacggttg tttttttctt ttttaaccaa aatgggcggt tttcgccccg aaaagagtgg   2280
gtggagtttt tgggtgaaaa aaggcggatt ttggggcatt gtggtactgc tggtagcatc   2340
```

```
gacgcatggg gccacgggac cgaagtcatc gtctcctccg gtgagtcttc aacccccccca   2400
aaactgccgc ggcgattttg gggcaaaatc gggcgatttt gggtcagtcg aagggggcgg   2460
tcggtccatc atttggggcc gggtgatttt tggggccgaa aagtgggaat ttggggccca   2520
atttggggcc caatttgggg ccaaatttgg gttttcgagg ggggattttt ttagggggag   2580
attttgggtc cccggagggg tttttgggtg gaaaaatggg gattttgggt cgttttgagg   2640
tggggttttt tggggtagaa atggcggtct gaggggaaaa tgtcgttttg gggccatttt   2700
gggccatttg aggggaaatt tgggtcaaaa aatgacgatt ttgggtcatt ttagggataa   2760
aaaatgaatt tagggagatt tgagggcaaa tttgggtcaa aaaatggtga tttggggtca   2820
aaaatggaca attttgggtc attttagggt taaaaatgga tttagggaaa tttgatggca   2880
aatttgggtc aaaaaatggt gattttgggt caaaaaatga ttattttggg tcattttagg   2940
gagaaaaatg aatttaggga gatttgaggg caaatttggg tcgaaaaatg gtgattttgg   3000
gtgaaaaatg gacaattttg ggtcatttta gggttaaaaa tgaatttagg gagattggac   3060
ggcaaatttg ggtcaaaaaa tggtgatttg gggtcaaaaa ataattattt tgggtcattt   3120
tagggataaa aaatgaattt agggagattt gagggcaaat ttgggtcgaa aaatggtgat   3180
tttgggtgaa aaatggacaa ttttgggtca ttttagggat aaaaaatgaa tttagggcga   3240
tttgagccaa atttgggtca aaaatggtga ttttgggtga aaaattgaca gttttgggtc   3300
attttagggt taaaaatgaa tttagggaga ttggacggca aatttgggtc aaaaaatggt   3360
gatttggggt caaaaaatga ttattttggg tcattttagg gataaaaaat gaatttaggg   3420
agatgtgagg gcaaatttgg gtcgaaaaat ggtgattttg ggtgaaaaat tgacagtttt   3480
gggtcatttt agggatataa atggacttag agagatttga gggcaaattt gggtgaaaaa   3540
atggacaatt tgggtcattt ttgggatata aatgaattta agatttgacg gcaaatttgg   3600
gtcaaaaaat ggtgatttgg gtcaaaaatg gtgattttgg ttgaaaaacg gccattttgg   3660
gtcattttag ggataaaaat gaatttaggg agatttgagg gcaaatttgg gtgaaaaaag   3720
ggcgatttgg gggtcatttt agggagaaaa atgaatttag ggcgatttga gggcaaattt   3780
gggtgaaaaa agggagattt ttggtcattt tagggataaa aatgaattta gggagaactg   3840
agggcaaatt tgggtcaaaa aatgacaatt tgggtcgttc tagggagaaa aatgaatttt   3900
gggcgatttg agggtaaatt tgggtcgaaa aatggtgatt tgggtcaaaa aatgattatt   3960
ttgggtcatt taagggagaa aagggattta gggagatttg agggcaaatt tgggtcgaaa   4020
aattgtgatt tggggtcaaa aaatgacaat tttgggtcat tttagggata taaatggact   4080
tagagcgatt tgagggcaaa tttgggtgaa aaaatgacaa tttgggtcat tttagggata   4140
taaatgaatt tagggcgatt tgagggcaaa tttggttcga aaatggtgat tttgggtcaa   4200
tttagggagg aaaatgaatt taaggcaatt tgaaggcaaa tttgggtgaa aaaatgacaa   4260
tttggggtca ttttaaagat aaaatgaatt tagggctatt tgagggcaaa tttgggtcaa   4320
aaaatggtga tttggggtca aaaaatatgg tgattttgag tcgttttagg ggggaaaatg   4380
aatttaggga gatttgaggg caaatttggg tcaaaaaatg gtgatttttg gtcgttttag   4440
tgataaaaaa tgaatttagg gcagtttgag ggcaaatctg ggtcaaaaaa gggtgatttt   4500
gagtcaaaaa tagtgatttt gggtcatttt agggatataa atgaattcag ggagatttga   4560
gggcaaattt gagtcaaaaa tagtgatatg ggtcaaaagt ggtgattttg gttgaaaaac   4620
agtcattttg ggtcatttta gggattaaaa tgaacttagg gagatttgag ggcaaatttg   4680
```

-continued ggtcaaaaaa tgacaatttt gggtcacttt acgaattaaa atgaattcag ggagatttga 4740
gggcaaattt gggtcaaaaa aatggtgatt ttgggtcatt ttagggttaa aaatgaattc 4800
aggatgattt gaaggcaact ttgggtcaaa aaaatgatta tttgggtcat tttaaagagg 4860
aaaatgaatt tagggagatt tgagggcaaa ttcgggtgaa aattggacaa ttttgggtca 4920
ttttagggat aaaaatgaat ttagggagat ttgagggcaa atttgggtca aaaaatggtg 4980
attttgggtc gttttaggaa taaaaatgaa tttagggaga tttgagggca aatttgggtc 5040
aaaaaatggt gatttggggt cattttcaga aggaaaatga ttattttccc cactaaaaat 5100
gtatattttg gggccaaatg gtgaaaaatg gtgattttta atcaaacgtc cccaaaattg 5160
gggaaatttc atcgatttga cccaaaattg agtttttttt ccctgttaaa aatgtacatt 5220
ttggggtcaa tcgttgaaat gttcccattt ttcacttctt tgcccccaaa ttttgctttc 5280
cggtgagaaa ttacagtgtt aattaattaa taatcggtaa ttgagcgaca attaataatt 5340
attaattaat taataggtcc ttttttggtg actccttcgc ttttggggcc aaaagtccat 5400
aaattggccc caaaaaatta atactgagta attggattcc aaagtattaa tgataaacat 5460
taaaagtgtt taattaatca tgatattaaa cataatttcg tttttattat cgatttatca 5520
acaacgatga acgataatac tttacaacaa tcgttaataa ttaattaatt aattaattaa 5580
ttaattaatt tctaataatt aattcgcatt atcggacacg agatgttgta atgattaata 5640
ataatttaat tcctaataat tagaagattc gttgaaaatt atctttacaa ataatcactt 5700
ctaataataa tgattaataa tagttaataa caataacaat aatgataata atattaataa 5760
tatgtgatat atttaatata aaattcgtat taatatatta tatctacaaa atatgatata 5820
aaatataata ttttatttat atataacaca atttattatc attattatca ttattaatat 5880
catcattatt aatgttatcg aaatacttat ttagaaataa taaaaacgga tttaataatg 5940
gcaacaaaaa tattttatta atgttaaaaa aaaataatta ataatttcca aagattcgaa 6000
ttcggggcaa cgaacggcac tcgataattt ttaattaatt aatagtttga attaatcggt 6060
actttttaat cctccatttt gcccgaaatc gccgtttttt gccccaaatt ccccaccgcg 6120
gcgttaaaaa cataaagaaa ttaagcttca aaagtgccct tttttggggt tgttttgacc 6180
ccccaaaaaa aatggccgaa ttgggggcgg ccgttttacg gttgggttca ttttgggttc 6240
aaaacagcca aaaatgggaa ctttgggttt cgaaaacaac aacaacaaaa aaacgggttt 6300
attttgggct cattttgggt gtttttgggt caggaggaga aaaaatagga agtttgagag 6360
cgaaacaacg gccgcttttg gggggaaaac ggcccttttt ggtcaacggc gggggaaaaa 6420
aaaaagcgga gtttttgggg tgaaaaagag cggttttggg taaatttggg ttttggggta 6480
aaagtggagg atttggggcg atgggagtta aaaaatgggt gtttttatgg gggttcggtg 6540
cagtttttcc tgtttgatgg ggggtttatt aatccggggg ggggaattaa tgagaattaa 6600
taatgttaat agaaatatct gggaaattaa tagcaattat taattgttaa tagttattaa 6660
tagttctata tatctcacat ctacgataca atataatatc gttataatca tatagtcgat 6720
atattacata taattatcag taataataat aagtaacaat aattagcagt aattaataat 6780
aataattaat agtattcgtt aataagatta ttgataataa ttaagtagta gtgattaata 6840
gagatgggat ttcgtgagaa atggaccaaa tttgggccgt tttgacccaa atttttggtg 6900
ggtttttttt ccgattcttt gtgaatttcg ggtcggattc atcagcaatt aattacggtt 6960
attaggggct attagaggct tttaattggg attattagag acttttaagc ggatttgggg 7020
acttttaagt ggattttatg attttttaag tggattttgg gtggatttta ccgcttttgg 7080

```
cgaattttaa tggggattat tagaagttat tagtggttat tagaagtaat tagaagccgt   7140
taggaatgat tagaaatgat tagaaattat tagaaatgat tagaaataat gagaaataat   7200
tagaaataat gagaaataat gagaaataat tagaaaaatg agaaataatg agaaataatg   7260
agaaataatt agaaaaatga gaaataagag gaatattaag tgaacatttt gtgattaatt   7320
acaaataatt gggaaatgag tagaaattat tagaaaatat tagaaataat cagaaaatta   7380
agtgaacatt ttgcgattaa ttagtgataa ttgggaaata attagaaata cttagaaata   7440
attaggaata agagaaatta ttagaaataa tacaaataat cagaaaataa tacaaataat   7500
tggaaataat cggaaataat cggaaaataa ttgaaataat gggaaacgat ggggaaatat   7560
tagaagcaat taagaaatta attgataaat tggaaataat gaggaattgt cagaaattaa   7620
tggaaataat ggggaaataa ttagaaatat tagaaataat cggaaaatta atgcaaatag   7680
ttggtaataa cgagaaataa gggggaaata atggaaataa tgggaaaata ttagaagcaa   7740
ttaagaaatt aattgataaa ttagaaacgt tgataaacaa tcggaaaata attgaaatgg   7800
aaataaatta gaaataattg gaaataatgg ggaaataatt agaaatatta gaaataatgg   7860
gaaatgatta agaaatatga gaaataatta gaaataatta gaaatattag aattaattaa   7920
tgggaaataa tgggaaataa tggcaaaata ttagaaataa cgggaaatga ttaagaaata   7980
atcagaaata attagaaata ttagaaataa ttaatgggaa ataatgggaa ataatggcaa   8040
aatattagaa ataatgggaa atgattaaga aatatgagaa ataattagaa ataattagaa   8100
atattagaaa taatggggaa ataacggaaa tagtgggaaa taatgggaaa atattagaaa   8160
taatgggaaa taattaagaa atattagaaa taattagaaa tattagaatt aattaacggg   8220
gaaataacgg aaataattgc aattattgga attatcgggg aaataattgg attaaaaaaa   8280
aattaattgg gggtccgtgg gagtaattaa ggatcgatcg atactgaatg atgagaaata   8340
attagcatta attaattaat tagttgatta attaaggggg acagatatta agaaatcaat   8400
cggggtttta taacagcaga aaacggaccg aaatgaccca aaaatgaccc ccccaaaaaa   8460
gattcctaat taagatccgg actcattaag cctcattatc cccctgataa ttagcactaa   8520
ttaacggggt tcattaatta gccccaatag cccgaatcgc cgctttttaa ttaataattc   8580
gtaatttttt tggcccaatt tggcctttt ccgaacggca ctttgggact cgttaagaaa   8640
tgagggcctt aatgagctta attagcggcg ctaattaagg cggttaatga aggtcaatga   8700
agggagggct gaggggaaat ggggccaata tggaccagta gggaccagta tggaccagta   8760
tagaccagta tggaccagta tggggttact gggaccagta cggaccagta tggatttacc   8820
ggaaccagta tagaccagta tagaccagta tggaccagta tggaccagta tgggtgcact   8880
gggaccagta tagaccagta tggaccagta tggaccagta tgggtgcact gggaccagta   8940
cagaccagta tggatttacc ggaaccagta tagaccagta tagaccagta tggaccagta   9000
tggggttact gggaccagta tagaccagta tagaccagta tagaccagta tggagcagta   9060
tggggggtca cctggagctg tactggtgcc ggtaccagta tgaaccagta tggactagta   9120
tgggtgcact ggaaccagta tagaccagta tggaccagta tggggaggtc gccgggagct   9180
gtactggttc ttactggtgc taggaccagt acggaccagt atggaccagt atagaccagt   9240
atgggtgcca atatggacca gtatggggtt gccgggagct gtactggttt gtactggtgc   9300
ctgtaccagt atagaccagt acggaccagt atggaccagt acggaggggt tgccgggagc   9360
tgtactggcg ccggtaccag tatggaccag tatagaccag tatgggtgca ctgggaccag   9420
```

-continued tatagaccag tatggaccag tatggggaag tgccgggagc tgtactggtg ctggtcccag 9480
tatggaccag tatggaccag tatggaccag taaggaccag tacgggttcc agtatggacc 9540
agtacggacc agtatggggg ggtgccgggt gctgtactgg tttgtactgg tgctggtgcc 9600
agtatagacc agtacggacc agtatggacc agtatggggg gtcacctgga gctgtactgg 9660
caccggtacc agtatggacc agtatggacc agtatgggtg cactgggacc agtacggacc 9720
agtacggggc gggggt 9736

<210> SEQ ID NO 16
<211> LENGTH: 18396
<212> TYPE: DNA
<213> ORGANISM: artificial sequence
<220> FEATURE:
<223> OTHER INFORMATION: Synthetic vector construct

<400> SEQUENCE: 16
ctaaattgta agcgttaata ttttgttaaa attcgcgtta aatttttgtt aaatcagctc 60 atttttaac caataggccg aaatcggcaa aatcccttat aaatcaaaag aatagaccga 120
gatagggttg agtgttgttc cagtttggaa caagagtcca ctattaaaga acgtggactc 180
caacgtcaaa gggcgaaaaa ccgtctatca gggcgatggc ccactacgtg aaccatcacc 240
ctaatcaagt tttttggggt cgaggtgccg taaagcacta aatcggaacc ctaaagggag 300
cccccgattt agagcttgac ggggaaagcc ggcgaacgtg gcgagaaagg aagggaagaa 360
agcgaaagga gcgggcgcta gggcgctggc aagtgtagcg gtcacgctgc gcgtaaccac 420
cacacccgcc gcgcttaatg cgccgctaca gggcgcgtcc cattcgccat tcaggctgcg 480
caactgttgg gaagggcgat cggtgcgggc ctcttcgcta ttacgccagc tggcgaaagg 540
gggatgtgct gcaaggcgat taagttgggt aacgccaggg ttttcccagt cacgacgttg 600
taaaacgacg gccagtgagc gcgcgtaata cgactcacta tagggcgaat tgggtaccgg 660
cgcgcctggg aaatttggcc ctcttggccc aattttgccc aaaaatggca aaatttgggg 720
tcatttcttc ccccgtaggt gagagcttca acctccagca gctccacgac tccaaaaaag 780
agacattttg cccattttct gccatttttt gacccaaatt ttggggtctt ttccccttcc 840
acggccactt tgaaacccta caaattactg cctctttttt tctccgtttt ttgccccaaa 900
tctgcctttt tttccccccct ttttggggcc ctccgggagg aaacgtctcc accggtggcc 960
gctcaagtgg tgaacccaca aactttgggg taaaaacaca ggattttggt caacgttgta 1020
tcactgtggg ttgtagtgct tacggttgtg gtgcttatca cggtgctcca tcccataaca 1080
aaaaccatcc tcattttggg gcaactttgg cccttttttgg tcaatttttg ccccccacgt 1140
acgacgattt ccccctcttc tttggccacc attgacccaa aatttggggt tattttcccc 1200
ctttttacca atattaccaa aaaaaaatca atttttccca tcttccccag accacaaaat 1260
tgggattttt ttttggcctt tttcggctat tttttgcccc aaaatccaac gattcccctc 1320
tcctcctcac ctccaaaaat ggggccattt tgtccctttt ccccattttc cacccccttt 1380
cccccccctc tccacattta cagtttttgg acgctcccaa tcttgccccg ttttgcccca 1440
aaatccccct ctttccaggc attcgatccc aaaattgaga tatttgatca tttttaacca 1500
ttttccccca aaataccgcc tcctcactga cggccgcggt gccaaaaacg gggaattttc 1560
tcccaaatac gttcaatgtt ttccctttttt ttgcccgttt ttgaccggtt ttgcccattt 1620
ttgtgcgttt ttaaccattt ttttttacat tttttaacca aatttgtgtg tttttacctt 1680
aagattcagc tcccatgggt gaaaaatgag aggtttctcc ccattcaaat tctacgactt 1740

-continued

```
ttgggatatc cctacgtgga gaatttgggg taaaaatgcc acaaatcggt taaaaatggc   1800
atttttggc taaaaaatgg catttttgt tctgaaaata gcattttttg gctaaaattg   1860
ggggttttag ccctaaaata gggaggaaaa caatgaggat ttgaaacact ccgtccccaa   1920
aattgaaatc tttgattctg gcatcattgg gtgatccgaa gtgaggaatt tggggtaaaa   1980
atggctcaaa ttggttaaaa ataaccgttt ttggtctgaa aatggcattt ttttggctaa   2040
aattggggtt tttagcccta aaatagggag gaaaacagtg aggatttgaa aactctgaac   2100
ccataaagtg aaatcctcaa ttttgggcat cattgggtga tcttaaggga ggaatttggg   2160
gcaaaaatgg ccaaattggt taagaatagc agtttttggt ctaaaaatgg catttttttgg   2220
ctaaaattgg ggtttttagc cctaaaatgg ggaggaatcc aatgaggatt tgaaacactc   2280
cgagcccaga attgaaatct tcgattttgg tcatctttgg gtgattctaa cggaggaatt   2340
tggggtaaaa acagcccaaa ttggttaaaa atggcagttt ttggtctaaa aatggcagtt   2400
tttgttctga aaatggcatt ttttggctaa aattggggtt ttttgcccta aaatagtgag   2460
gaaaacaaca aggatttgaa aaacctgaag gcaaacaatg aaatcttcga ttttgggcca   2520
atattgcagg aatttggagc gaaggatggc caaaaaacgg ttgttttttt ctttttttaac   2580
caaaatgggc ggttttcgcc ccgagctagc ataacttcgt atagcataca ttatacgaag   2640
ttataagcgt aatctggaac atcgtatgta ccggatccga agcaggcttt cctggaaggt   2700
cctggaaggg ggcgtccgcg ggagctcacg gggacagccc ccccccaaag cccccaggga   2760
tgtaattacg tccctccccc gctagggggc agcagcgagc cgcccggggc tccgctccgg   2820
tccggcgctc cccccgcatc cccgagccgg cagcgtgcgg ggacagcccg ggcacgggga   2880
aggtggcacg ggatcgcttt cctctgaacg cttctcgctg ctctttgagc ctgcagacac   2940
ctggggggat acggggaaaa agctttaggc tgagaagcag gctttcctgg aaggtcctgg   3000
aagggggcgt ccgcgggagc tcacggggac agcccccccc caaagccccc agggatgtaa   3060
ttacgtccct cccccgctag gggggcagcag cgagccgccc ggggctccgc tccggtccgg   3120
cgctcccccc gcatccccga gccggcagcg tgcggggaca gcccgggcac ggggaaggtg   3180
gcacgggatc gctttcctct gaacgcttct cgctgctctt tgagcctgca gacacctggg   3240
gggatacggg gaaaaagctt taggctgaac tagctagtct cgaggtcgag gtgagcccca   3300
cgttctgctt cactctcccc atctcccccc cctccccacc cccaattttg tatttattta   3360
ttttttaatt attttgtgca gcgatggggg cggggggggg gggggcgcgc gccaggcggg   3420
gcggggcggg gcgaggggcg gggcggggcg aggcggagag gtgcggcggc agccaatcag   3480
agcggcgcgc tccgaaagtt tccttttatg gcgaggcggc ggcggcggcg gccctataaa   3540
aagcgaagcg cgcggcgggc gggagtcgct gcgttgcctt cgccccgtgc cccgctccgc   3600
gccgcctcgc gccgcccgcc ccggctctga ctgaccgcgt tactcccaca ggtgagcggg   3660
cgggacggcc cttctcctcc gggctgtaat tagcgcttgg tttaatgacg gctcgtttct   3720
tttctgtggc tgcgtgaaag ccttaaaggg ctccgggagg gccctttgtg cggggggggag   3780
cggctcgggg ggtgcgtgcg tgtgtgtgtg cgtggggagc gccgcgtgcg gcccgcgctg   3840
cccggcggct gtgagcgctg cgggcgcggc gcggggcttt gtgcgctccg cgtgtgcgcg   3900
aggggagcgc ggccgggggc ggtgccccgc ggtgcggggg ggctgcgagg ggaacaaagg   3960
ctgcgtgcgg ggtgtgtgcg tggggggggtg agcagggggt gtgggcgcgg cggtcgggct   4020
gtaacccccc cctgcacccc cctccccgag ttgctgagca cggcccggct tcgggtgcgg   4080
```

-continued

```
ggctccgtgc ggggcgtggc gcggggctcg ccgtgccggg cggggggtgg cggcaggtgg 4140
gggtgccggg cggggcgggg ccgcctcggg ccggggaggg ctcgggggag gggcgcggcg 4200
gccccggagc gccggcggct gtcgaggcgc ggcgagccgc agccattgcc ttttatggta 4260
atcgtgcgag agggcgcagg gacttccttt gtcccaaatc tggcggagcc gaaatctggg 4320
aggcgccgcc gcaccccctc tagcgggcgc gggcgaagcg gtgcggcgcc ggcaggaagg 4380
aaatgggcgg ggagggcctt cgtgcgtcgc cgcgccgccg tccccttctc catctccagc 4440
ctcggggctg ccgcaggggg acggctgcct tcgggggggga cggggcaggg cggggttcgg 4500
cttctggcgt gtgaccggcg gctctagagc ctctgctaac catgttcatg ccttcttctt 4560
tttcctacag ctcctgggca acgtgctggt tgttgtgctg tctcatcatt ttggcaaaga 4620
attatcgcat gcctgcgtcg acggtaccgc gggcccggga tccaccggtc gccaccatgg 4680
tgagcaaggg cgaggagctg ttcaccgggg tggtgcccat cctggtcgag ctggacggcg 4740
acgtaaacgg ccacaagttc agcgtgtccg gcgagggcga gggcgatgcc acctacggca 4800
agctgaccct gaagttcatc tgcaccaccg gcaagctgcc cgtgccctgg cccaccctcg 4860
tgaccaccct gacctacggc gtgcagtgct tcagccgcta ccccgaccac atgaagcagc 4920
acgacttctt caagtccgcc atgcccgaag gctacgtcca ggagcgcacc atcttcttca 4980
aggacgacgg caactacaag acccgcgccg aggtgaagtt cgagggcgac accctggtga 5040
accgcatcga gctgaagggc atcgacttca aggaggacgg caacatcctg gggcacaagc 5100
tggagtacaa ctacaacagc cacaacgtct atatcatggc cgacaagcag aagaacggca 5160
tcaaggtgaa cttcaagatc cgccacaaca tcgaggacgg cagcgtgcag ctcgccgacc 5220
actaccagca gaacaccccc atcggcgacg gccccgtgct gctgcccgac aaccactacc 5280
tgagcaccca gtccgccctg agcaaagacc ccaacgagaa gcgcgatcac atggtcctgc 5340
tggagttcgt gaccgccgcc gggatcactc tcggcatgga cgagctgtac aagtaaagcg 5400
gccggccgcg actctagatc ataatcagcc ataccacatt tgtagaggtt ttacttgctt 5460
taaaaaacct cccacacctc cccctgaacc tgaaacataa aatgaatgca attgttgttg 5520
ttaacttgtt tattgcagct tataatggtt acaaataaag caatagcatc acaaatttca 5580
caaataaagc atttttttca ctgcattcta gttgtggttt gtccaaactc atcaatgtat 5640
cttaaggaac cccttcctcg acattgatta ttgactagct agttattaat agtaatcaat 5700
tacggggtca ttagttcata gcccatatat ggagttccgc gttacataac ttacggtaaa 5760
tggcccgcct ggctgaccgc ccaacgaccc ccgcccattg acgtcaataa tgacgtatgt 5820
tcccatagta acgccaatag ggactttcca ttgacgtcaa tgggtggact atttacggta 5880
aactgcccac ttggcagtac atcaagtgta tcatatgcca agtacgcccc ctattgacgt 5940
caatgacggt aaatggcccg cctggcatta tgcccagtac atgaccttat gggactttcc 6000
tacttggcag tacatctacg tattagtcat cgctattacc atgggtcgag gtgagcccca 6060
cgttctgctt cactctcccc atctcccccc cctccccacc cccaattttg tatttattta 6120
tttttaatt attttgtgca gcgatggggg cgggggggggg gggggcgcgc gccaggcggg 6180
gcggggcggg gcgaggggcg gggcggggcg aggcggagag gtgcggcggc agccaatcag 6240
agcggcgcgc tccgaaagtt tccttttatg gcgaggcggc ggcggcggcg gccctataaa 6300
aagcgaagcg cgcggcgggc gggagtcgct gcgttgcctt cgccccgtgc cccgctccgc 6360
gccgcctcgc gccgcccgcc ccggctctga ctgaccgcgt tactcccaca ggtgagcggg 6420
cgggacggcc cttctcctcc gggctgtaat tagcgcttgg tttaatgacg gctcgtttct 6480
```

-continued

```
tttctgtggc tgcgtgaaag ccttaaaggg ctccgggagg gccctttgtg cggggggggag   6540
cggctcgggg ggtgcgtgcg tgtgtgtgtg cgtggggagc gccgcgtgcg gcccgcgctg   6600
cccggcggct gtgagcgctg cgggcgcggc gcggggcttt gtgcgctccg cgtgtgcgcg   6660
aggggagcgc ggccgggggc ggtgccccgc ggtgcggggg ggctgcgagg ggaacaaagg   6720
ctgcgtgcgg ggtgtgtgcg tgggggggtg agcagggggt gtgggcgcgg cggtcgggct   6780
gtaacccccc cctgcacccc cctccccgag ttgctgagca cggcccggct tcgggtgcgg   6840
ggctccgtgc ggggcgtggc gcggggctcg ccgtgccggg cggggggtgg cggcaggtgg   6900
gggtgccggg cggggcgggg ccgcctcggg ccggggaggg ctcgggggag ggcgcggcg   6960
gccccggagc gccggcggct gtcgaggcgc ggcgagccgc agccattgcc ttttatggta   7020
atcgtgcgag agggcgcagg gacttccttt gtcccaaatc tggcggagcc gaaatctggg   7080
aggcgccgcc gcaccccctc tagcgggcgc gggcgaagcg gtgcggcgcc ggcaggaagg   7140
aaatgggcgg ggagggcctt cgtgcgtcgc cgcgccgccg tccccttctc catctccagc   7200
ctcggggctg ccgcaggggg acggctgcct tcggggggga cggggcaggg cggggttcgg   7260
cttctggcgt gtgaccggcg gctctagagc ctctgctaac catgttcatg ccttcttctt   7320
tttcctacag ctcctgggca acgtgctggt tattgtgctg tctcatcatt ttggcaaaga   7380
attcctagcg ccaccatgac cgagtacaag cctaccgtgc gcctggccac tcgcgatgat   7440
gtgccccgcg ccgtccgcac tctggccgcc gctttcgccg actaccccgc tacccggcac   7500
accgtggacc ccgaccggca catcgagcgt gtgacagagt tgcaggagct gttcctgacc   7560
cgcgtcgggc tggacatcgg caaggtgtgg gtagccgacg acggcgcggc cgtggccgtg   7620
tggactaccc ccgagagcgt tgaggccggc gccgtgttcg ccgagatcgg cccccgaatg   7680
gccgagctga gcggcagccg cctggccgcc cagcagcaaa tggagggcct gcttgccccc   7740
catcgtccca aggagcctgc ctggtttctg gccactgtag gagtgagccc cgaccaccag   7800
ggcaagggct tgggcagcgc cgtcgtgttg cccggcgtag aggccgccga acgcgccggt   7860
gtgcccgcct ttctcgaaac aagcgcacca agaaaccttc cattctacga gcgcctgggc   7920
ttcaccgtga ccgccgatgt cgaggtgccc gagggaccta ggacctggtg tatgacacga   7980
aaacctggcg cctaatgatc tagaaccggt catggccgca ataaaatatc tttattttca   8040
ttacatctgt gtgttggttt tttgtgtgtt cgaacctgca gcccggggga tccgaagcag   8100
gctttcctgg aaggtcctgg aagggggcgt ccgcgggagc tcacggggac agcccccccc   8160
caaagccccc agggatgtaa ttacgtccct cccccgctag gggcagcag cgagccgccc   8220
ggggctccgc tccggtccgg cgctcccccc gcatccccga gccggcagcg tgcggggaca   8280
gcccgggcac ggggaaggtg gcacgggatc gctttcctct gaacgcttct cgctgctctt   8340
tgagcctgca gacacctggg gggatacggg gaaaaagctt taggctgaga agcaggcttt   8400
cctggaaggt cctggaaggg ggcgtccgcg ggagctcacg gggacagccc ccccccaaag   8460
cccccaggga tgtaattacg tccctccccc gctagggggc agcagcgagc cgcccggggc   8520
tccgctccgg tccggcgctc ccccgcatc cccgagccgg cagcgtgcgg ggacagcccg   8580
ggcacgggga aggtggcacg ggatcgcttt cctctgaacg cttctcgctg ctctttgagc   8640
ctgcagacac ctggggggat acggggaaaa agctttaggc tgaactagaa tgcatataac   8700
ttcgtatagc atacattata cgaagttatg gatcccccaa atcaatctaa agtatatatg   8760
agtaacctga ggctatggca gggcctgccg ccccgacgtt ggctgcgagc cctgggcctt   8820
```

-continued

```
cacccgaact tggggggtgg ggtggggaaa aggaagaaac gcgggcgtat tggccccaat   8880
ggggtctcgg tggggtatcg acagagtgcc agccctggga ccgaaccccg cgtttatgaa   8940
caaacgaccc aacaccgtgc gttttattct gtctttttat tgccgtcata gcgcgggttc   9000
cttccggtat tgtctccttc cgtgtttcag ttagcctccc cctagggtgg gcgaagaact   9060
ccagcatgag atccccgcgc tggaggatca tccagccggc gtcccggaaa acgattccga   9120
agcccaacct ttcatagaag gcggcggtgg aatcgaaatc tcgtgatggc aggttgggcg   9180
tcgcttggtc ggtcatttcg aaccccagag tcccgctcag aagaactcgt caagaaggcg   9240
atagaaggcg atgcgctgcg aatcgggagc ggcgataccg taaagcacga ggaagcggtc   9300
agcccattcg ccgccaagct cttcagcaat atcacgggta gccaacgcta tgtcctgata   9360
gcggtccgcc acacccagcc ggccacagtc gatgaatcca gaaaagcggc cattttccac   9420
catgatattc ggcaagcagg catcgccatg ggtcacgacg agatcctcgc cgtcgggcat   9480
gctcgccttg agcctggcga acagttcggc tggcgcgagc ccctgatgct cttcgtccag   9540
atcatcctga tcgacaagac cggcttccat ccgagtacgt gctcgctcga tgcgatgttt   9600
cgcttggtgg tcgaatgggc aggtagccgg atcaagcgta tgcagccgcc gcattgcatc   9660
agccatgatg gatactttct cggcaggagc aaggtgagat gacaggagat cctgccccgg   9720
cacttcgccc aatagcagcc agtcccttcc cgcttcagtg acaacgtcga gcacagctgc   9780
gcaaggaacg cccgtcgtgg ccagccacga tagccgcgct gcctcgtctt gcagttcatt   9840
cagggcaccg gacaggtcgg tcttgacaaa aagaaccggg cgcccctgcg ctgacagccg   9900
gaacacggcg gcatcagagc agccgattgt ctgttgtgcc cagtcatagc cgaatagcct   9960
ctccacccaa gcggccggag aacctgcgtg caatccatct tgttcaatca tgcgaaacga  10020
tcctcatcct gtctcttgat cgattacgcc cccaactgag agaactcaaa ggttacccca  10080
gttggggcac actagtggcg gtctgagggg aaaatgtcgt tttggggcca ttttgggcca  10140
tttgagggga aatttgggtc aaaaaatgac gattttgggt cattttaggg ataaaaaatg  10200
aatttaggga gatttgaggg caaatttggg tcaaaaaatg gtgatttggg gtcaaaaatg  10260
gacaattttg ggtcatttta gggttaaaaa tggatttagg gaaatttgat ggcaaatttg  10320
ggtcaaaaaa tggtgatttt gggtcaaaaa atgattattt tgggtcattt tagggagaaa  10380
aatgaattta gggagatttg agggcaaatt tgggtcgaaa aatggtgatt ttgggtgaaa  10440
aatggacaat tttgggtcat tttagggtta aaaatgaatt tagggagatt ggacggcaaa  10500
tttgggtcaa aaaatggtga tttggggtca aaaaataatt attttgggtc attttaggga  10560
taaaaaatga atttagggag atttgagggc aaatttgggt cgaaaaatgg tgattttggg  10620
tgaaaaatgg acaattttgg gtcattttag ggataaaaaa tgaatttagg gcgatttgag  10680
ccaaatttgg gtcaaaaatg gtgattttgg gtgaaaaatt gacagttttg ggtcatttta  10740
gggttaaaaa tgaatttagg gagattggac ggcaaatttg ggtcaaaaaa tggtgatttg  10800
gggtcaaaaa atgattattt tgggtcattt tagggataaa aaatgaattt agggagatgt  10860
gagggcaaat ttgggtcgaa aaatggtgat tttgggtgaa aaattgacag ttttgggtca  10920
ttttagggat ataaatggac ttagagagat ttgagggcaa atttgggtga aaaaatggac  10980
aatttgggtc atttttggga tataaatgaa tttaagattt gacggcaaat ttgggtcaaa  11040
aaatggtgat ttgggtcaaa aatggtgatt ttggttgaaa aacggccatt ttgggtcatt  11100
ttagggataa aaatgaattt agggagattt gagggcaaat ttgggtgaaa aaagggcgat  11160
ttgggggtca ttttagggag aaaaatgaat ttagggcgat ttgagggcaa atttgggtga  11220
```

aaaaagggag atttttggtc attttaggga taaaaatgaa tttagggaga actgagggca 11280
aatttgggtc aaaaaatgac aatttgggtc gttctaggga gaaaaatgaa ttttgggcga 11340
tttgagggta aatttgggtc gaaaaatggt gatttgggtc aaaaaatgat tattttgggt 11400
catttaaggg agaaaaggga tttagggaga tttgagggca aatttgggtc gaaaaattgt 11460
gatttggggt caaaaaatga caattttggg tcattttagg gatataaatg gacttagagc 11520
gatttgaggg caaatttggg tgaaaaaatg acaatttggg tcattttagg gatataaatg 11580
aatttagggc gatttgaggg caaatttggt tcgaaaatgg tgattttggg tcaatttagg 11640
gaggaaaatg aatttaaggc aatttgaagg caaatttggg tgaaaaaatg acaatttggg 11700
gtcattttaa agataaaatg aatttagggc tatttgaggg caaatttggg tcaaaaaatg 11760
gtgatttggg gtcaaaaaat atggtgattt tgagtcgttt tagggggaa aatgaattta 11820 gggagatttg agggcaaatt tgggtcaaaa aatggtgatt tttggtcgtt ttagtgataa 11880
aaaatgaatt tagggcagtt tgagggcaaa tctgggtcaa aaaagggtga ttttgagtca 11940
aaaatagtga ttttgggtca ttttagggat ataaatgaat tcagggagat ttgagggcaa 12000
atttgagtca aaaatagtga tatgggtcaa aagtggtgat tttggttgaa aaacagtcat 12060
tttgggtcat tttagggatt aaaatgaact tagggagatt tgagggcaaa tttgggtcaa 12120
aaaatgacaa ttttgggtca ctttacgaat taaaatgaat tcagggagat ttgagggcaa 12180
atttgggtca aaaaaatggt gattttgggt catttttaggg ttaaaaatga attcaggatg 12240
atttgaaggc aactttgggt caaaaaaatg attatttggg tcattttaaa gaggaaaatg 12300
aatttaggga gatttgaggg caaattcggg tgaaaattgg acaattttgg gtcattttag 12360
ggataaaaat gaatttaggg agatttgagg gcaaatttgg gtcaaaaaat ggtgattttg 12420
ggtcgtttta ggaataaaaa tgaatttagg gagatttgag ggcaaatttg ggtcaaaaaa 12480
tggtgatttg gggtcatttt cagaaggaaa atgattattt tccccactaa aaatgtatat 12540
tttggggcca aatggtgaaa aatggtgatt tttaatcaaa cgtccccaaa attggggaaa 12600
tttcatcgat ttgacccaaa attgagtttt ttttccctgt taaaaatgta cattttgggg 12660
tcaatcgttg aaatgttccc atttttcact tctttgcccc caaattttgc tttccggtga 12720
gaaattacag tgttaattaa ttaataatcg gtaattgagc gacaattaat aattattaat 12780
taattaatag gtcctttttt ggtgactcct tcgcttttgg ggccaaaagt ccataaattg 12840
gccccaaaaa attaatactg agtaattgga ttccaaagta ttaatgataa acattaaaag 12900
tgtttaatta atcatgatat taaacataat ttcgttttta ttatcgattt atcaacaacg 12960
atgaacgata atactttaca acaatcgtta ataattaatt aattaattaa ttaattaatt 13020
aatttctaat aattaattcg cattatcgga cacgagatgt tgtaatgatt aataataatt 13080
taattcctaa taattagaag attcgttgaa aattatcttt acaaataatc acttctaata 13140
ataatgatta ataatagtta ataacaataa caataatgat aataatatta ataatatgtg 13200
atatatttaa tataaaattc gtattaatat attatatcta caaaatatga tataaaatat 13260
aatattttat ttatatataa cacaatttat tatcattatt atcattatta atatcatcat 13320
tattaatgtt atcgaaatac ttatttagaa ataataaaaa cggatttaat aatggcaaca 13380
aaaatatttt attaatgtta aaaaaaaata attaataatt tccaaagatt cgaattcggg 13440
gcaacgaacg gcactcgata atttttaatt aattaatagt ttgaattaat cggtactttt 13500
taatcctcca ttttgcccga aatcgccgtt ttttgcccca aattccccac cgcggcgtta 13560

-continued

```
aaaacataaa gaaattaagc ttcaaaagtg cccttttttg gggttgtttt gacccccccaa  13620
aaaaaatggc cgaattgggg gcggccgttt tacggttggg ttcattttgg gttcaaaaca  13680
gccaaaaatg ggaactttgg gtttcgaaaa caacaacaac aaaaaaacgg gtttattttg  13740
ggctcatttt gggtgttttt gggtcaggag gagaaaaaat aggaagtttg agagcgaaac  13800
aacggccgct tttgggggga aaacggccct ttttggtcaa cggcggggga aaaaaaaaag  13860
cggagttttt ggggtgaaaa agagcggttt tgggtaaatt tgggttttgg ggtaaaagtg  13920
gaggatttgg ggcgatggga gttaaaaaat gggtgttttt atgggggttc ggtgcagttt  13980
ttcctgtttg atggggggtt tattaatccg gggggggggaa ttaatgagaa ttaataatgt  14040
taatagaaat atctgggaaa ttaatagcaa ttattaattg ttaatagtta ttaatagttc  14100
tatatatctc acatctacga tacaatataa tatcgttata atcatatagt cgatatatta  14160
catataatta tcagtaataa taataagtaa caataattag cagtaattaa taataataat  14220
taatagtatt cgttaataag attattgata ataattaagt agtagtgatt aatagagatg  14280
ggatttcgtg agaaatggac caaatttggg ccgttttgac ccaaattttt ggtgggtttt  14340
ttttccgatt ctttgtgaat ttcgggtcgg attcatcagc aattaattac ggttattagg  14400
ggctattaga ggcttttaat tgggattatt agagactttt aagcggattt ggggactttt  14460
aagtggattt tatgattttt taagtggatt ttgggtggat tttaccgctt ttggcgaatt  14520
ttaatgggga ttattagaag ttattagtgg ttattagaag taattagaag ccgttaggaa  14580
tgattagaaa tgattagaaa ttattagaaa tgattagaaa taatgagaaa taattagaaa  14640
taatgagaaa taatgagaaa taattagaaa aatgagaaat aatgagaaat aatgagaaat  14700
aattagaaaa atgagaaata agaggaatat taagtgaaca ttttgtgatt aattacaaat  14760
aattgggaaa tgagtagaaa ttattagaaa atattagaaa taatcagaaa attaagtgaa  14820
cattttgcga ttaattagtg ataattggga aataattaga aatacttaga aataattagg  14880
aataagagaa attattagaa ataatacaaa taatcagaaa ataatacaaa taattggaaa  14940
taatcggaaa taatcggaaa ataattgaaa taatgggaaa cgatggggaa atattagaag  15000
caattaagaa attaattgat aaattggaaa taatgaggaa ttgtcagaaa ttaatggaaa  15060
taatggggaa ataattagaa atattagaaa taatcggaaa attaatgcaa atagttggta  15120
ataacgagaa ataaggggga aataatggaa ataatgggaa aatattagaa gcaattaaga  15180
aattaattga taaattagaa acgttgataa acaatcggaa aataattgaa atggaaataa  15240
attagaaata attggaaata atggggaaat aattagaaat attagaaata atgggaaatg  15300
attaagaaat atgagaaata attagaaata attagaaata ttagaattaa ttaatgggaa  15360
ataatgggaa ataatggcaa aatattagaa ataacgggaa atgattaaga aataatcaga  15420
aataattaga aatattagaa ataattaatg ggaaataatg ggaaataatg gcaaaatatt  15480
agaaataatg ggaaatgatt aagaaatatg agaaataatt agaaataatt agaaatatta  15540
gaaataatgg ggaaataacg gaaatagtgg gaaataatgg gaaaatatta gaaataatgg  15600
gaaataatta agaaatatta gaaataatta gaaatattag aattaattaa cggggaaata  15660
acggaaataa ttgcaattat tggaattatc ggggaaataa ttggattaaa aaaaaattaa  15720
ttgggggtcc gtgggagtaa ttaaggatcg atcgatactg aatgatgaga aataattagc  15780
attaattaat taattagttg attaattaag ggggacagat attaagaaat caatcggggt  15840
tttataacag cagaaaacgg accgaaatga cccaaaaatg acccccccaa aaaagattcc  15900
taattaagat ccggactcat taagcctcat tatccccctg ataattagca ctaattaacg  15960
```

```
gggttcatta attagcccca atagcccgaa tcgccgcttt ttaattaata attcgtaatt  16020
tttttggccc aatttgggcc ttttccgaac ggcactttgg gactcgttaa gaaatgaggg  16080
ccttaatgag cttaattagc ggcgctaatt aaggcggtta atgaaggtca atgaagggag  16140
ggctgagggg aaatggggcc aatatgcggc cgcggccgcc accgcggtgg agctccagct  16200
tttgttccct ttagtgaggg ttaattgcgc gcttggcgta atcatggtca tagctgtttc  16260
ctgtgtgaaa ttgttatccg ctcacaattc cacacaacat acgagccgga agcataaagt  16320
gtaaagcctg gggtgcctaa tgagtgagct aactcacatt aattgcgttg cgctcactgc  16380
ccgctttcca gtcgggaaac ctgtcgtgcc agctgcatta atgaatcggc caacgcgcgg  16440
ggagaggcgg tttgcgtatt gggcgctctt ccgcttcctc gctcactgac tcgctgcgct  16500
cggtcgttcg gctgcggcga gcggtatcag ctcactcaaa ggcggtaata cggttatcca  16560
cagaatcagg ggataacgca ggaaagaaca tgtgagcaaa aggccagcaa aaggccagga  16620
accgtaaaaa ggccgcgttg ctggcgtttt tccataggct ccgcccccct gacgagcatc  16680
acaaaaatcg acgctcaagt cagaggtggc gaaacccgac aggactataa agataccagg  16740
cgtttccccc tggaagctcc ctcgtgcgct ctcctgttcc gaccctgccg cttaccggat  16800
acctgtccgc ctttctccct tcgggaagcg tggcgctttc tcatagctca cgctgtaggt  16860
atctcagttc ggtgtaggtc gttcgctcca agctgggctg tgtgcacgaa ccccccgttc  16920
agcccgaccg ctgcgcctta tccggtaact atcgtcttga gtccaacccg gtaagacacg  16980
acttatcgcc actggcagca gccactggta acaggattag cagagcgagg tatgtaggcg  17040
gtgctacaga gttcttgaag tggtggccta actacggcta cactagaagg acagtatttg  17100
gtatctgcgc tctgctgaag ccagttacct tcggaaaaag agttggtagc tcttgatccg  17160
gcaaacaaac caccgctggt agcggtggtt tttttgtttg caagcagcag attacgcgca  17220
gaaaaaaagg atctcaagaa gatcctttga tcttttctac ggggtctgac gctcagtgga  17280
acgaaaactc acgttaaggg attttggtca tgagattatc aaaaaggatc ttcacctaga  17340
tccttttaaa ttaaaaatga agttttaaat caatctaaag tatatatgag taaacttggt  17400
ctgacagtta ccaatgctta atcagtgagg cacctatctc agcgatctgt ctatttcgtt  17460
catccatagt tgcctgactc cccgtcgtgt agataactac gatacgggag ggcttaccat  17520
ctggccccag tgctgcaatg ataccgcgag acccacgctc accggctcca gatttatcag  17580
caataaacca gccagccgga agggccgagc gcagaagtgg tcctgcaact ttatccgcct  17640
ccatccagtc tattaattgt tgccgggaag ctagagtaag tagttcgcca gttaatagtt  17700
tgcgcaacgt tgttgccatt gctacaggca tcgtggtgtc acgctcgtcg tttggtatgg  17760
cttcattcag ctccggttcc caacgatcaa ggcgagttac atgatccccc atgttgtgca  17820
aaaaagcggt tagctccttc ggtcctccga tcgttgtcag aagtaagttg gccgcagtgt  17880
tatcactcat ggttatggca gcactgcata attctcttac tgtcatgcca tccgtaagat  17940
gcttttctgt gactggtgag tactcaacca agtcattctg agaatagtgt atgcggcgac  18000
cgagttgctc ttgcccggcg tcaatacggg ataataccgc gccacatagc agaactttaa  18060
aagtgctcat cattggaaaa cgttcttcgg ggcgaaaact ctcaaggatc ttaccgctgt  18120
tgagatccag ttcgatgtaa cccactcgtg cacccaactg atcttcagca tcttttactt  18180
tcaccagcgt ttctgggtga gcaaaaacag gaaggcaaaa tgccgcaaaa aagggaataa  18240
gggcgacacg gaaatgttga atactcatac tcttcctttt tcaatattat tgaagcattt  18300
```

-continued

```
atcagggtta ttgtctcatg agcggataca tatttgaatg tatttagaaa aataaacaaa  18360

taggggttcc gcgcacattt ccccgaaaag tgccac                            18396
```